United States Patent
Nie et al.

(10) Patent No.: US 8,420,155 B2
(45) Date of Patent: Apr. 16, 2013

(54) ALLOYED SEMICONDUCTOR QUANTUM DOTS AND CONCENTRATION-GRADIENT ALLOYED QUANTUM DOTS, SERIES COMPRISING THE SAME AND METHODS RELATED THERETO

(75) Inventors: Shuming Nie, Atlanta, GA (US); Robert E. Bailey, Sacramento, CA (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 13/157,099

(22) Filed: Jun. 9, 2011

(65) Prior Publication Data
US 2011/0311453 A1 Dec. 22, 2011

Related U.S. Application Data

(63) Continuation of application No. 10/555,729, filed as application No. PCT/US2004/013119 on Apr. 28, 2004, now Pat. No. 7,981, 667.

(60) Provisional application No. 60/468,729, filed on May 7, 2003.

(51) Int. Cl.
*C23C 14/54* (2006.01)
(52) U.S. Cl.
USPC ............ 427/10; 436/164; 436/166; 436/172; 422/82.05; 422/82.08; 435/7.1; 435/287.1; 356/925
(58) Field of Classification Search ........................ None
See application file for complete search history.

(56) References Cited

U.S. PATENT DOCUMENTS

| 5,087,616 | A | 2/1992 | Meyers et al. |
|---|---|---|---|
| 6,207,392 | B1 | 3/2001 | Weiss et al. |
| 6,306,610 | B1 | 10/2001 | Bawendi et al. |
| 6,710,366 | B1 | 3/2004 | Lee et al. |
| 6,846,565 | B2 | 1/2005 | Korgel et al. |
| 2003/0047816 | A1 | 3/2003 | Dutta |
| 2003/0066998 | A1 | 4/2003 | Lee |

OTHER PUBLICATIONS

Bailey et al., Alloyed semiconductor quantum dots: tuning the optical properties without changing the particle size, 2003 J Am Chem Soc, 125: pp. 7100-7106.*

(Continued)

*Primary Examiner* — N. C. Yang
(74) *Attorney, Agent, or Firm* — Leydig, Voit & Mayer, Ltd.

(57) ABSTRACT

An alloyed semiconductor quantum dot comprising an alloy of at least two semiconductors, wherein the quantum dot has a homogeneous composition and is characterized by a band gap energy that is non-linearly related to the molar ratio of the at least two semiconductors; a series of alloyed semiconductor quantum dots related thereto; a concentration-gradient quantum dot comprising an alloy of a first semiconductor and a second semiconductor, wherein the concentration of the first semiconductor gradually increases from the core of the quantum dot to the surface of the quantum dot and the concentration of the second semiconductor gradually decreases from the core of the quantum dot to the surface of the quantum dot; a series of concentration-gradient quantum dots related thereto; in vitro and in vivo methods of use; and methods of producing the alloyed semiconductor and concentration-gradient quantum dots and the series of quantum dots related thereto.

14 Claims, 11 Drawing Sheets

OTHER PUBLICATIONS

Aldana et al., "Photochemical instability of CdSe nanocrystals coated by hydrophilic thiols," J. Am. Chem. Soc., 123, 8844-8850 (2001).

Alivisatos, "Perspectives on the physical chemistry of semiconductor nanocrystals," J. Phys. Chem., 100, 13226-13229 (1996).

Alivisatos, Semiconductor clusters, nanocrystals, and quantum dots, Science, 271:5251, 933-37 (1996).

Bailey et al., "Allowed semiconductor quantum dots: Tuning the optical properties without changing the particle size," J. Am. Chem. Soc., 125(23): 7100-7106 (2003).

Bernard et al., "Electronic structure of ZnS, ZnSe, ZnTe, and their pseudobinary alloys," Physical Review B, 36:3, 3199-3228 (1987).

Chan et al., "Quantum dot bioconjugates for ultrasensitive nonisotopic detection," Science, 281, 2016-2018 (1998).

Dabbousi et al., "(CdSe)ZnS core-shell quantum dots: synthesis and characterization of a size series of highly luminescent nanocrystallites," J. Phys. Chem., B, 101: 9463-9475 (1997).

De Smet et al., "Determination of Ostwad ripening rates from dynamic light scattering measurements," Langmuir, 15, 2327-2332 (1999).

Golan et al., "Epitaxial size control by mismatch tuning in electrodeposited Cd(Se,Te) quantum dots on {111} gold," Adv. Materials VCH Verlagsgesellschaft, 8(8): 631-633 (1996).

Gurusinghe et al., "Composition tunable properties of $CdS_xTe_{1-x}$ alloys," J. Phys. Chem., 112: 12795-12800 (2008).

Hines et al., "Synthesis and characterization of strongly luminescing ZnS-capped CdSe nanocrystals," J. Phys. Chem., 100, 468-71 (1996).

Korgel et al., "Controlled synthesis of mixed core and layered (Zn,Cd)S and (Hg,Cd)S nanocrystals within phosphatidylcholine vesicles," Langmiur, 16, 3588-3594 (2000).

Link et al., "Alloy formation of gold-silver nanoparticles and the dependence of the plasmon absorption on their composition," J. Phys. Chem. B., 103, 3529-3533 (1999).

Mallin et al., "Solution-phase synthesis of sub-10 nm Au-Ag alloy nanoparticles," American Chemical Society, 2:11, 1235-1237 (2002).

Mitchell et al., "Programmed assembly of DNA functionalized quantum dots," J. Am. Chem. Soc., 121, 8122-8123 (1999).

Mulvaney, "Surface plasmon spectroscopy of nanosized metal particles," Langmiur, 12, 788-800 (1996).

Nirmal et al., "Fluorescence intermittency in single cadmium selenide nanocrystals," Nature, 383, 802-804 (1996).

Peng et al., "Epitaxial growth of highly luminescent CdSe/CdS core/shell nanocrystals with photostability and electronic accessibility," J. Am. Chem. Soc., 119, 7019-1029 (1997).

Peng et al., "Formation of high-quality CdTe, CdSe, and CdS nanocrystals using CdO as precursor," J. Am. Chem. Soc., 123, 183-184 (2001).

Peng et al., "Kinetics of II-VI and III-V colloidal semiconductor nanocrystals growth: 'focusing' of size distributions," J. Am. Chem. Soc., 120, 5343-5344 (1998).

Poon et al., "Relativistic band structure of ternary II-VI semiconductor alloys containing Cd, Zn, Se and Te," J. Phys.: Condens. Matter 7, 2783-2799 (1995).

Talapin et al., "Synthesis and surface modification of amino-stabilized CdSe, CdTe and InP nanocrystals," Colloids Surf., 202, 145-154 (2002).

U.S. Patent & Trademark Office, International Search Report in International Patent Application No. PCT/US2004/013119 (Mar. 10, 2006).

Wei et al., "First-principles calculation of band offsets, optical bowings and defects in CdS, CdSe, CdTe, and their alloys," J. Appl. Phys., 87:3, 1304-1311 (2000).

Weller, "Colloidal semiconductor Q-Particle: Chemistry in the transition region between solid state and molecules," Angew. Chem. Int. Ed. Engl., 32, 41-53 (1993).

Zhu et al., "Electronic bandgap and refractive index dispersion on single crystalline epitaxial ZuGeN2," Mat. Res. Soc. Symp. Proc., 607: 291-296 (2000).

* cited by examiner

ALLOYED SEMICONDUCTOR QUANTUM DOTS AND CONCENTRATION-GRADIENT ALLOYED QUANTUM DOTS, SERIES COMPRISING THE SAME AND METHODS RELATED THERETO

CROSS-REFERENCE TO RELATED APPLICATIONS

This patent application is a continuation of copending U.S. patent application Ser. No. 10/555,729, filed Dec. 21, 2006, which is a national stage application of International Patent Application No. PCT/US04/13119, filed Apr. 28, 2004, which claims the benefit of U.S. Provisional Patent Application No. 60/468,729, filed May 7, 2003, which is incorporated by reference.

STATEMENT REGARDING FEDERALLY SPONSORED RESEARCH AND DEVELOPMENT

This invention was made with Government support under Grant Number GM060562 awarded by the National Institutes of Health. The United States Government has certain rights in the invention.

FIELD OF THE INVENTION

This invention pertains to alloyed semiconductor quantum dots, concentration-gradient alloyed quantum dots, series of either of the foregoing, methods of producing the same and methods of using the same.

BACKGROUND OF THE INVENTION

Quantum dots, which are spherical semiconductor nanocrystals, are of considerable current interest due to their unique size-dependent properties that are not available from either discrete atoms or bulk solids (Alivisatos, *J. Phys. Chem.* 100: 13226-13239 (1996); Nirmal et al., *Acc. Chem. Res.* 32: 407-414 (1999); and Eychmüller, *J. Phys. Chem. B* 32:104:6514-6528 (2000)). Recent research has demonstrated the wide spectral ranges over which the photoluminescence (PL) of various nanocrystalline materials can be tuned simply by changing the particle size (Murray et al., *J. Am. Chem. Soc.* 115: 8706-8715 (1993); Hines et al., *J. Phys. Chem.* 100: 468-471 (1996); Mićić et al., *J. Phys. Chem.* 101: 4904-4912 (1997); Harrison et al., *J. Mater. Chem.* 9: 2721-2722 (1999); and Talapin et al., *J. Phys. Chem. B* 105: 2260-2263 (2001)). Other properties of interest are high quantum efficiencies, narrow and symmetric emission profiles, wide optical absorption bands, and large molar absorptivities. Furthermore, several groups have shown that these highly luminescent nanocrystals can be conjugated to biological molecules such as proteins and nucleic acids for multicolor biolabeling and biosensing (Bruchez et al., *Science* 281: 2013-2016 (1998); Chan et al., *Science* 281: 2016-2018 (1998); Mitchell et al., *J. Am. Chem. Soc.* 121: 8122-8123 (1999), Mattoussi et al., *J. Am. Chem. Soc.* 122: 12142-12150 (2000); Pathak et al., *J. Am. Chem. Soc.* 123: 4103-4104 (2001); Dubertret et al., *Science* 298: 1759-1762 (2002); Jaiswal et al., *Nat. Biotechnol.* 21: 47-51 (2003); Wu et al., *Nat. Biotechnol.* 21: 41-46 (2003); Åkerman et al., *Proc. Natl. Acad. Sci. USA* 99: 12617-12621 (2002); and Murphy, *Anal. Chem.* 74: 520A-526A (2002)). However, current studies are primarily based on binary semiconductor materials where the emission wavelength is tuned by changing the particle size from about 1 nm to 8 nm. As a result, the largest nanocrystals are expected to have 512 times the volume and 64 times the surface area of the smallest particles. These large differences could cause major problems in bioconjugation and surface chemistry, as well as in the binding and reaction kinetics of nanocrystals to target molecules.

Korgel et al. overcomes some of these problems by generating a series of quantum dots comprising an alloy of $Zn_yCd_{1-y}S$ or $Hg_yCd_{1-y}S$ that, within each series, are fixed in size and composition-tunable (Korgel et al., *Langmuir* 16: 3588-3594 (2000)). However, each of the quantum dots has a band gap energy that is linearly related to the molar ratio of the semiconductors comprising the quantum dots. The optical properties of these quantum dots, therefore, are still limited in that the range of emission peak wavelengths of the series of the quantum dots is confined to the range of wavelengths defined by the corresponding pure, non-alloyed semiconductor quantum dots, i.e., by the quantum dots consisting of pure HgS, pure CdS, or pure ZnS. Therefore, improved quantum dots comprising an alloy of semiconductors and having unique optical properties that are not limited to the emission peak wavelength range set by the pure, non-alloyed forms are needed in the art.

The invention provides such improved quantum dots, as well as series related thereto, methods of producing either of the foregoing and methods of using either of the foregoing. These and other advantages of the invention, as well as additional inventive features, will be apparent from the description of the invention provided herein.

BRIEF SUMMARY OF THE INVENTION

The present invention provides an alloyed semiconductor quantum dot comprising an alloy of at least two semiconductors, wherein the quantum dot has a homogeneous composition and is characterized by a band gap energy that is non-linearly related to the molar ratio of the at least two semiconductors.

The present invention also provides a series of alloyed semiconductor quantum dots, wherein each alloyed semiconductor quantum dot of the series comprises an alloy of at least two semiconductors and has a homogeneous composition, wherein the size of each quantum dot is within about 5% of the size of the average-sized quantum dot, wherein each of the alloyed semiconductor quantum dots of the series comprise the same alloy, but varies in molar ratio of the at least two semiconductors, and wherein at least one of the alloyed semiconductor quantum dots of the series is characterized by a band gap energy that is non-linearly related to the molar ratio of the at least two semiconductors.

Further provided by the present invention is an alloyed semiconductor quantum dot comprising an alloy of at least two semiconductors, wherein the quantum dot has an emission peak wavelength that is not within the range of wavelengths defined by the emission peak wavelengths of the quantum dots consisting of only one of the at least two semiconductors.

The present invention further provides a concentration-gradient quantum dot comprising an alloy of a first semiconductor and a second semiconductor, wherein the concentration of the first semiconductor gradually increases from the core of the quantum dot to the surface of the quantum dot and the concentration of the second semiconductor gradually decreases from the core of the quantum dot to the surface of the quantum dot.

Also provided by the present invention is a series of concentration-gradient quantum dots, wherein each quantum dot comprises an alloy of a first semiconductor and a second semiconductor, wherein, for each quantum dot, the concentration of the first semiconductor gradually increases from the core of the quantum dot to the surface of the quantum dot and the concentration of the second semiconductor gradually decreases from the core of the quantum dot to the surface of the quantum dot, wherein the gradient by which the concentration of the first semiconductor increases and the gradient by which the concentration of the second semiconductor decreases from the core of the quantum dot to the surface of the quantum dot varies among the quantum dots of the series, wherein the size of each quantum dot is within about 5% of the size of the average-sized quantum dot, and wherein each quantum dot comprises the same semiconductors.

The present inventive quantum dots are useful in a number of in vitro and in vivo methods, particularly in the instance that the quantum dots are conjugated to a biological agent, such as a biomolecule. These methods are further provided by the present invention. In this regard, the present invention provides a method of detecting a target in a sample. The method comprises (i) contacting a sample with an alloyed semiconductor quantum dot or a concentration-gradient quantum dot, either of which is conjugated to a biological agent, wherein the biological agent specifically binds to a target in the sample, (ii) allowing the biological agent to specifically bind to the target, and (iii) analyzing the sample via spectroscopy, thereby obtaining a spectroscopic signature of the sample, wherein the spectroscopic signature is indicative of the presence or the absence of the target in the sample.

The present invention also provides a method of detecting the location of a target within a sample. The method comprises (i) contacting a sample with an alloyed semiconductor quantum dot or a concentration-gradient quantum dot, either of which is conjugated to a biological agent, wherein the biological agent specifically binds to a target in the sample, (ii) allowing the biological agent to specifically bind to the target, and (iii) imaging the sample or a section thereof, thereby detecting the location of the target within the sample.

Also provided by the present invention is a method of monitoring a biological process in vitro. The method comprises (i) contacting a sample with an alloyed semiconductor quantum dot or a concentration-gradient quantum dot, either of which is conjugated to a biological agent, wherein the biological agent specifically binds to a target in the sample, wherein the target functions in a biological process, (ii) allowing the biological agent to specifically bind to the target, and (iii) imaging the sample or a section thereof over a period of time or before and after a stimulus, thereby monitoring a biological process in vitro.

The present invention provides a method of detecting the location of a target in vivo. The method comprises (i) administering to a host an alloyed semiconductor quantum dot or a concentration-gradient quantum dot, either of which is conjugated to a biological agent, wherein the biological agent specifically binds to a target in the host, (ii) allowing the biological agent to specifically bind to the target, (iii) imaging the host, a section thereof, or a cell thereof, thereby detecting the location of the target in vivo.

The present invention provides a method of monitoring a biological process in vivo. The method comprises (i) administering to a host an alloyed semiconductor quantum dot or a concentration-gradient quantum dot, either of which is conjugated to a biological agent, wherein the biological agent specifically binds to a target in the host, wherein the target functions in a biological process, (ii) allowing the biological agent to specifically bind to the target, and (iii) imaging the host, a section, or a cell thereof over a period of time or before and after a stimulus, thereby monitoring a biological process in vivo.

Likewise the present inventive series of quantum dots are useful in a number of in vitro and in vivo methods, especially in the case that each of the quantum dots of the series is conjugated to a different biological agent, such that each of the different biological agents corresponds to a quantum dot having a unique molar ratio of the at least two semiconductors. In this regard, the present invention also provides a method of detecting more than one target in a sample. The method comprises (i) contacting a sample with a series of alloyed semiconductor quantum dots or a series of concentration-gradient quantum dots, wherein each of the quantum dots of either series is conjugated to a different biological agent, wherein each of the biological agents specifically bind to a different target in the sample, (ii) allowing the biological agents to specifically bind to the targets, and (iii) analyzing the sample via spectroscopy, thereby obtaining a spectroscopic signature of the sample, wherein the spectroscopic signature is indicative of the presence or absence of the more than one target in the sample.

The present invention also provides a method of detecting the location of more than one target within a sample. The method comprises (i) contacting a sample with a series of alloyed semiconductor quantum dots or a series of concentration-gradient quantum dots, wherein each of the quantum dots of either series is conjugated to a different biological agent, wherein each of the biological agents specifically binds to a different target in the sample, (ii) allowing the biological agents to specifically bind to the targets, (iii) imaging the sample or a section thereof, thereby detecting the location of the more than one target within the sample.

Further provided by the present invention is a method of monitoring a biological process in vitro. The method comprises (i) contacting a sample with a series of alloyed semiconductor quantum dots or a series of concentration-gradient quantum dots, wherein each of the quantum dots of either series is conjugated to a different biological agent, wherein each of the biological agents specifically binds to a different target in the sample, wherein each of the targets functions in a biological process, (ii) allowing the biological agents to specifically bind to the targets, and (iii) imaging the sample or a section thereof over a period of time or before and after a stimulus, thereby monitoring a biological process in vitro.

A method of detecting the location of more than one target in vivo is provided by the present invention. The method comprises (i) administering to a host a series of alloyed semiconductor quantum dots or a series of concentration-gradient quantum dots, wherein each of the quantum dots of either series is conjugated to a different biological agent, wherein each of the biological agents specifically binds to a different target in the host, (ii) allowing the biological agents to specifically bind to the targets, (iii) imaging the host, a section thereof, or a cell thereof, thereby detecting the location of the more than one target in vivo.

The present invention also provides a method of monitoring a biological process in vivo. The method comprises (i) administering to a host a series of alloyed semiconductor quantum dots or a series of concentration-gradient quantum dots, wherein each of the quantum dots of either series is conjugated to a different biological agent, wherein each of the biological agents specifically binds to a different target in the host, wherein each of the targets functions in a biological process, (ii) allowing the biological agents to specifically bind to the targets, and (iii) imaging the host, a sample thereof, or a section thereof over a period of time or before and after a stimulus, thereby monitoring a biological process in vivo.

The present invention further provides methods of producing the quantum dots of the present invention and methods of producing the series comprising the quantum dots of the present invention. In this respect, the present invention also provides a method of producing a quantum dot comprising an alloy of at least two semiconductors. The method comprises (i) providing a first solution under conditions which allow nanocrystal formation to take place, (ii) providing a second solution comprising precursors of the at least two semiconductors at a molar ratio under conditions which do not allow nanocrystal formation to take place, (iii) adding the second solution to the first solution, thereby allowing nanocrystal formation to take place, and (iv) changing the conditions to conditions that halt further nanocrystal growth and formation. Upon this method, a quantum dot comprising an alloy of at least two semiconductors is produced.

Further provided by the present invention is a method of producing a ternary alloyed semiconductor quantum dot comprising an alloy of two semiconductors AB and AC, wherein A is a species that is common to the two semiconductors and B and C are each a species that is found in one of the two semiconductors. The method comprises (i) providing a first solution under conditions which allow nanocrystal formation to take place, (ii) providing a second solution comprising A, B, and C under conditions which do not allow nanocrystal formation to take place, wherein A is present in the second solution at concentration that is reaction-limiting, (iii) adding the second solution to the first solution, thereby allowing nanocrystal formation to take place, (iv) changing the conditions to conditions that halt nanocrystal growth and formation.

The present invention also provides a method of producing a series of ternary alloyed semiconductor quantum dots, wherein each quantum dot comprises an alloy of two semiconductors AB and AC, wherein A is a species that is common to the two semiconductors and B and C are each a species that is found in one of the two semiconductors. The method comprises (i) providing a first solution under conditions which allow nanocrystal formation to take place, (ii) providing a second solution comprising A, B, and C at a molar ratio under conditions which do not allow nanocrystal formation to take place, wherein A is present in the second solution at concentration that is reaction-limiting, (iii) adding the second solution to the first solution, thereby allowing nanocrystal formation to take place, (iv) changing the conditions to conditions that halt nanocrystal growth and formation, and (v) repeating steps (i)-(iv) at least one time, thereby producing at least one other quantum dot in the series, wherein each time the molar ratio of A, B, and C is different from the molar ratio of A, B, and C of the other quantum dots of the series.

A method of producing a ternary concentration-gradient quantum dot comprising a first semiconductor AB and a second semiconductor AC, wherein A is a species that is common to the first semiconductor and the second semiconductor and B and C are each a species found in only one of the first semiconductor and the second semiconductor, is also provided by the present invention. The method comprises (i) providing a first solution under conditions which allow nanocrystal formation to take place, (ii) providing a second solution comprising A, B, and C at a molar ratio under conditions which do not allow nanocrystal formation to take place, wherein each of B and C are present in the second solution at a concentration that is reaction-limiting, (iii) adding the second solution to the first solution, thereby allowing nanocrystal formation to take place, and (iv) changing the conditions to conditions that halt nanocrystal growth and formation.

The present invention provides a method of producing a series of ternary concentration-gradient quantum dots, wherein each of the quantum dots comprise a first semiconductor AB and a second semiconductor AC, wherein A is a species that is common to the first semiconductor and the second semiconductor and B and C are each a species found in only one of the first semiconductor and the second semiconductor. The method comprises (i) providing a first solution under conditions which allow nanocrystal formation to take place, (ii) providing a second solution comprising A, B, and C at a molar ratio under conditions which do not allow nanocrystal formation to take place, wherein each of B and C are present in the second solution at a concentration that is reaction-limiting, (iii) adding the second solution to the first solution, thereby allowing nanocrystal formation to take place, (iv) changing the conditions that allow nanocrystal formation to conditions that halt nanocrystal growth and formation, and (v) repeating steps (i)-(iv) at least one time, thereby producing at least one other quantum dot of the series, wherein each time the molar ratio of A, B, and C is different from the molar ration of A, B, and C of the other quantum dots of the series.

DETAILED DESCRIPTION OF THE INVENTION

Figure 1:
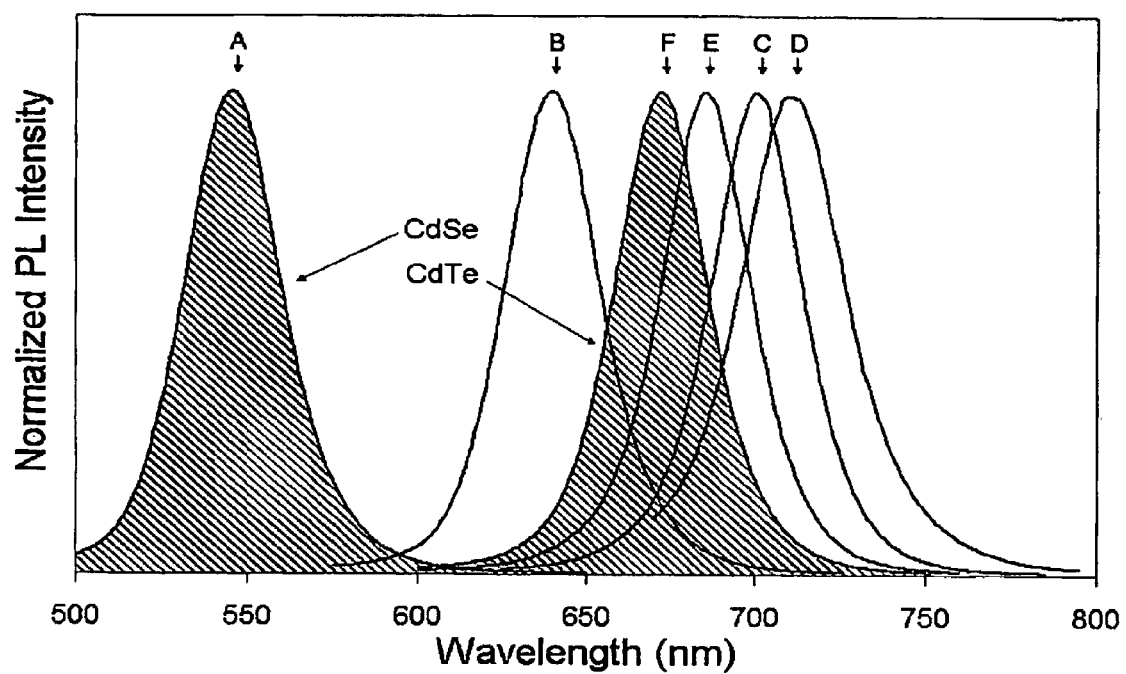
FIG. 1: Photoluminescence spectra of $CdSe_{1-x}Te_x$ nanocrystals at a fixed size of 2.9±0.3 nm (mean diameter) for compositions ranging from pure CdSe to pure CdTe. (A) x=0, (B) x=0.20, (C) x=0.37, (D) x=0.62, (E) x=0.91, (F) x=1.0.

The present invention provides an alloyed semiconductor quantum dot comprising an alloy of at least two semiconductors, wherein the quantum dot has a homogeneous composition and is characterized by a band gap energy that is non-linearly related to the molar ratio of the at least two semiconductors.

Further provided by the present invention is an alloyed semiconductor quantum dot comprising an alloy of at least two semiconductors, wherein the quantum dot has an emission peak wavelength that is not within the range of wavelengths defined by the emission peak wavelengths of the quantum dots consisting of only one of the at least two semiconductors.

The present invention further provides a concentration-gradient quantum dot comprising an alloy of a first semiconductor and a second semiconductor, wherein the concentration of the first semiconductor gradually increases from the core of the quantum dot to the surface of the quantum dot and the concentration of the second semiconductor gradually decreases from the core of the quantum dot to the surface of the quantum dot.

The term "quantum dot" as used herein refers to a single spherical nanocrystal of semiconductor material where the radius of the nanocrystal is less than or equal to the size of the exciton Bohr radius for that semiconductor material (the value for the exciton Bohr radius can be calculated from data found in handbooks containing information on semiconductor properties, such as the *CRC Handbook of Chemistry and Physics*, 83rd ed., Lide, David R. (Editor), CRC Press, Boca Raton, Fla. (2002)). Quantum dots are known in the art, as they are described in references, such as Weller, *Angew. Chem. Int. Ed. Engl.* 32: 41-53 (1993), Alivisatos, *J. Phys. Chem.* 100: 13226-13239 (1996), and Alivisatos, *Science* 271: 933-937 (1996).

Description of the Alloy and the Semiconductors

The alloyed semiconductor quantum dots of the present invention or of the present inventive series of alloyed semiconductor quantum dots comprise an alloy of at least two semiconductors. The term "alloyed" as used herein means that the two or more semiconductors form a completely amalgamated solid wherein the two or more semiconductors are randomly distributed throughout the solid. Also, in this respect, the term "alloy" as used herein refers to any solid which is a product of an almagamation process. "Semiconductor" as used herein means any material that exhibits a finite band gap energy in the range of about 0.01 eV to about 10 eV. The concentration-gradient quantum dots of the present invention or of the present inventive series of concentration-gradient quantum dots comprise an alloy of a first semiconductor and a second semi-conductor, wherein the composition of the quantum dot changes gradually from pure material of the first semiconductor at the center to pure material of the second semiconductor at the surface as a function of the radius of the quantum dot.

The at least two semiconductors of the alloyed semiconductor quantum dots, as well as the first semiconductor and second semiconductor of the concentration-gradient quantum dot, can be any semiconductors, so long as the semiconductors are alloyable. By "alloyable" as used herein is meant that the semiconductor materials comprising the quantum dot are capable of forming an amalgamated solid wherein the semiconductors are randomly distributed throughout the solid. Furthermore, one of ordinary skill in the art realizes that each of the at least two semiconductors of the alloyed semiconductor quantum dots is a different semiconductor from the other(s). Likewise, one of ordinary skill in the art realizes that each of the first semiconductor and second semiconductor of the concentration-gradient quantum dot is different from the other.

With respect to the alloyed semiconductor quantum dots described herein, it is preferable that each of the at least two semiconductors has a lattice parameter that is within about 10% of the mean lattice parameter. The term "lattice parameter" as used herein refers to the physical dimensions, i.e. length, of the sides of the unit cell of the crystalline material. Also, with respect to the concentration-gradient quantum dots described herein, it is preferable that each of the first semiconductor and second semiconductor of the concentration-gradient quantum dot has a lattice parameter that is within about 10% of the mean lattice parameter. By "lattice parameter that is within about 10% of the mean lattice parameter" as used herein is meant that the lattice parameter of the individual semiconductor is the same as the mean lattice parameter ±10%. By "mean lattice parameter" as used herein refers to the average value of the lattice parameters of each semiconductor comprising the quantum dot. Such semiconductors are known in the art, including for instance, $CdS_{1-x}Se_x$, $CdS_{1-x}Te_x$, $CdSe_{1-x}Te_x$, $Zn_{1-x}Cd_xS$, $Zn_{1-x}Cd_xSe$, $Zn_{1-x}Cd_xTe$, $In_{1-x}Ga_xAs$ and $In_{1-x}Ga_xP$, wherein x is any fraction between 0 and 1. Furthermore, methods of determining the percent by which the lattice parameter of a semiconductor varies from the mean lattice parameter are known in the art. See, for instance, the *CRC Handbook of Chemistry and Physics*, 83rd ed., Lide, David R. (Editor), CRC Press, Boca Raton, Fla. (2002), which tabulates the lattice parameter values for many semiconductor materials With respect to the alloyed semiconductor quantum dots described herein, it is preferable that at least one of the at least two semiconductors of the alloyed semiconductor quantum dot is a Group II-Group VI semiconductor or a Group III-Group V semiconductor. Likewise, with respect to the concentration gradient quantum dots described herein, it is preferable that at least one of the first semiconductor and second semiconductor of the concentration-gradient quantum dot is a Group II-Group VI semiconductor or a Group III-Group V semiconductor. By "Group II-Group VI semiconductor" as used herein, is meant a semiconductor made from one Group II element and from one Group VI element of the Periodic Table of the Elements wherein "Group II" and "Group VI" refer to the traditional numbering system of the Periodic Table of the Elements. Likewise, the term "Group III-Group V semiconductor" as used herein refers to a semiconductor made from one Group III element and from one Group V element from the Periodic Table of the Elements wherein "Group III" and "Group V" refer to the traditional numbering system of the Periodic Table of the Elements. Group II-Group VI and Group III-Group V semiconductors are known in the art and include, for instance, $CdS_{1-x}Se_x$, $CdS_{1-x}Te_x$, $CdSe_{1-x}Te_x$, $ZnSe_{1-x}Te_x$, $Zn_{1-x}Cd_xTe$, $Cd_{1-x}Hg_xS$, $Cd_{1-x}Hg_xTe$, $Ga_xAs$, $Ga_{1-x}Al_xAs$ and $In_{1-x}Ga_xP$. With respect to the present invention, preferred Group II-Group VI and Group III-Group V semiconductors are $CdSe_{1-x}Te_x$, $ZnSe_{1-x}Te_x$, $Zn_{1-x}Cd_xTe$, $Cd_{1-x}Hg_xS$, $Cd_{1-x}Hg_xTe$, $Ga_xAs$, and $In_{1-x}Ga_xP$, wherein x is any fraction between 0 and 1.

The molar ratio of the semiconductors comprising the quantum dots described herein can be any molar ratio, such that the molecular formula of the quantum dot can reflect any molar ratio. However, in the instance that the alloy of any of the present inventive quantum dots comprises CdSSe, it is preferred that the alloy has a molecular formula $CdS_{1-x}Se_x$, wherein x is any fraction between 0 and 1. Also, in the instance that the alloy of any of the quantum dots described herein comprises CdSTe, it is preferred that the alloy has a molecular formula $CdS_{1-x}Te_x$, wherein x is any fraction between 0 and 1. In the instance that the alloy of any of the quantum dots described herein comprises ZnSeTe, it is preferred that the alloy has a molecular formula $ZnSe_{1-x}Te_x$, wherein x is any fraction between 0 and 1. In the case that the alloy of any of the quantum dots described herein comprises ZnCdTe, it is preferred that the alloy has a molecular formula $Zn_{1-x}Cd_xTe$, wherein x is any fraction between 0 and 1. When the alloy of any of the quantum dots described herein comprises CdHgS, it is preferable that the alloy has a molecular formula $Cd_{1-x}Hg_xS$, wherein x is any fraction between 0 and 1. In the instance that the alloy comprises CdSeTe, it is preferred that the alloy has a molecular formula $CdSe_{1-x}Te_x$, wherein x is any fraction between 0 and 1.

With respect to the alloyed semiconductor quantum dots described herein, it is also preferred that at least one of the at least two semiconductors of the alloyed semiconductor quantum dot is a compound semiconductor. By "compound semiconductor" as used herein is meant a semiconductor comprising at least two different elements from the Periodic Table of the Elements. Furthermore, with respect to the concentration-gradient quantum dots described herein, it is preferred that at least one of the first semiconductor and second semiconductor of the concentration-gradient quantum dot is a compound semiconductor. Preferred compound semiconductors for any of the present inventive quantum dots include, for instance, ZnS, ZnSe, ZnTe, CdS, CdSe, CdTe, HgS, HgSe, HgTe, GaP, GaAs, InP and InAs. The at least two semiconductors of the alloyed semiconductor quantum dot are preferably CdSe and CdTe. Likewise, the alloy of the concentration-gradient quantum dot described herein preferably comprises CdSe and CdTe.

Description of the Composition Type

The alloyed semiconductor quantum dots of the present invention or of the series comprising the same have a homogeneous composition. By "homogeneous composition" is meant that the quantum dot has a uniform composition throughout the entire quantum dot, such that the composition is the same with respect to the semiconductors comprising the quantum dot and the molar ratio of the semiconductors comprising the quantum dot, i.e., the quantum dot is uniform in composition from core to surface.

Unlike the alloyed semiconductor quantum dots of the present invention, the concentration-gradient quantum dots described herein comprising an alloy of a first semiconductor and a second semiconductor do not have a homogeneous composition. Rather, the concentration of the first semiconductor gradually increases from the core of the quantum dot to the surface of the quantum dot, while the concentration of the second semiconductor gradually decreases from the core of the quantum dot to the surface of the quantum dot. The term "core" as used herein refers to the center point of the quantum dot. The term "surface" as used herein means the exterior layer of the quantum dot.

Description of the Size

The alloyed semiconductor quantum dots of the present invention or of the present inventive series of alloyed semiconductor quantum dots, as well as the concentration-gradient quantum dots of the present invention or of the present inventive series of concentration-gradient dots, can have any diameter, and, thus, be of any size, provided that the radius of the quantum dot is less than or equal to the Bohr exciton radius for the material from which the quantum dot is composed. Preferably, the quantum dots described herein are less than 15 nm in diameter. More preferably, the quantum dots described herein are less than 8 nm in diameter.

Optical Properties of the Quantum Dots

The present inventive alloyed semiconductor quantum dots have unique optical properties. Specifically, the emission peak wavelength of the alloyed semiconductor quantum dot is not within the range of wavelengths defined by the emission peak wavelengths of the quantum dots consisting of only one of the at least two semiconductors. For instance, if the alloyed semiconductor quantum dot comprised an alloy of two semiconductors, CdSe and CdTe, the emission peak wavelength of the quantum dot would be outside the range of wavelengths set by the emission peak wavelength of a quantum dot consisting solely of CdSe and the emission peak wavelength of a quantum dot consisting solely of CdTe. As emission peak wavelength is related to the absorbance peak wavelength, the same can be said of the present inventive alloyed semiconductor quantum dots with respect to absorbance peak wavelength, i.e., the absorbance peak wavelength of the alloyed semiconductor quantum dot is not within the range of wavelengths defined by the absorbance peak wavelengths of the quantum dots consisting of only one of the at least two semiconductors. Without being held to any particular theory, the present inventive alloyed semiconductor quantum dots have these unique optical properties due to the non-linear relationship between the band gap energy and the molar ratio of the at least two semiconductors, which comprise the quantum dot. The term "band gap energy" as used herein refers to the lowest energy at which a quantum dot will absorb or emit photons. The actual value of this "band gap energy" can be calculated by the equation $E=hc/\lambda$, where E is the band gap energy, h is Plank's constant (a fundamental physical constant of nature), c is the speed of light in vacuum (a fundamental physical constant of nature) and $\lambda$ is the wavelength of the photon absorbed or emitted by the quantum dot. Methods of determining whether or not a quantum dot has a band gap energy that is non-linearly related to the molar ratio of the semiconductors comprising it are known in the art. See, for instance, and also Example 4 set forth below. One of ordinary skill in the art appreciates that the unique properties of the present inventive quantum dots allow some of them to be particularly useful for methods that require the detection of a larger range of emission peak wavelengths. Also, the unique optical properties of the present inventive quantum dots allow them to be useful for methods that require the detection of emission peak wavelengths found in the near infrared or far red spectrum.

Description of a Quantum Yield

The present inventive quantum dots can be of any quantum yield. The term "quantum yield" as used herein means refers to the efficiency with which the quantum dot converts absorbed photons into luminescence. If, for example, every photon absorbed produces a photon attributed to luminescence, then the quantum yield is 100%. However, if only one photon attributed to luminescence is emitted for every 10 absorbed photons, then the quantum yield is 10%, and so on. One of ordinary skill in the art appreciates that, in general, the higher the quantum yield, the higher the optical efficiency is, such that quantum dots with high quantum yields are desirable. Preferably, the quantum yield of any of the quantum dots described herein is at least 15%. More preferably, the quantum yield is within the range of about 30% and about 60%, and most preferably, the quantum yield is within the range of about 40% and about 60%.

Conjugated and Encapsulated Quantum Dots

The quantum dots of the present invention or of the present inventive series of quantum dots can be conjugated to a biological agent. By "conjugated" as used herein means that the quantum dot is attached to a biological agent through any means, e.g., chemical bonds, electrostatic interactions, cross-linkers, and the like. As used herein the term "biological agent" refers to any molecule, entity, or part of either of the foregoing, that is endogeneous to a whole organism and/or is biologically active within a whole organism. Suitable biological agents for conjugation to the present inventive quantum dots are known in the art and include, for instance, a biomolecule or a drug. Preferably, the biological agent is a biomolecule, wherein "biomolecule" refers to any molecule or part thereof that is naturally-occurring within or on the body of a whole organism. Preferred biomolecules for conjugation to the present inventive quantum dots include a protein, a peptide, a nucleic acid molecule, a combination thereof, and the like. Also preferred is that the biological agent is a drug, wherein "drug" as used herein refers to any chemical agent that is exogenous to the body of a whole organism and typically is synthesized by means known in the art. The quantum dots described herein can be conjugated to any drug. The drug may or may not be therapeutically effective to any organism. In this regard, the quantum dots may be conjugated to a candidate drug wherein one of ordinary skill in the appropriate art reasonably believes that the candidate drug may have a therapeutic or beneficial effect to any whole organism.

The quantum dots of the present invention or of the present inventive series of quantum dots can have a semiconductor shell, i.e., can be encapsulated within a shell comprising a semiconductor. By "semiconductor shell" as used herein refers to a thin layer of semiconductor material (typically 1-10 atomic layers thick) deposited on the outer surface of the quantum dot; this "semiconductor shell" being composed of a different semiconductor material than the quantum dot itself. The semiconductor shell can comprise any semiconductor. Preferably, the semiconductor shell comprises ZnS, CdS, CdSe, CdTe, GaAs, or AlGaAs. Likewise, the quantum dots of the present invention or of the present inventive series of quantum dots can be encapsulated within a polymer bead. The polymer bead can comprise any polymer. Preferably, the polymer bead comprises a polymer, such as polystyrene, brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinyl acetate, polyvinyl chloride, polyvinyl pyridine, polyvinylbenzyl chloride, polyvinyl toluene, polyvinylidene chloride, polydivinylbenzene, polymethylmethacrylate, polylactide, polyglycolide, poly(lactide-co-glycolide), polyanhydride, polyorthoester, polyphosphazene, polysulfone, or a combination or a copolymer thereof.

Description of the Series of Quantum Dots

The present invention also provides a series of alloyed semiconductor quantum dots. As used herein, the term "series" refers to a group of quantum dots. A series of quantum dots is not limited to any particular number of individual quantum dots. In this regard, the series can comprise any number of quantum dots, provided that the number of dots in the series is greater than one. Each alloyed semiconductor quantum dot of the present inventive series of alloyed semiconductor quantum dots comprises an alloy of at least two semiconductors and has a homogeneous composition. Also, the size of each alloyed semiconductor quantum dot of the series is within about 5% of the size of the average-sized quantum dot. The term "average-sized quantum dot" as used herein refers to the quantum dot having the size that is equivalent to the average of all of the sizes of the quantum dots of a given series. The average-sized quantum dot may or may not actually exist as a quantum dot of the series. The phrase "within about 5% of the size of the average-sized quantum dot" as used herein means that the quantum dots of the series are essentially equivalent in size ±5% of the size of the average-sized quantum dot. Each of the alloyed semiconductor quantum dots of the series comprise the same alloy, but varies in molar ratio of the at least two semiconductors, i.e., the quantum dots have the same chemical composition with regard to the semiconductors comprising them, but each of the quantum dots have a different molar ratio of the semiconductors comprising it. For example, for a given series of quantum dots comprising CdTe and CdSe, all of the quantum dots comprise CdSeTe. However, the molar ratio of one dot of the series may be 1:1, whereas the molar ratio of another quantum dot may be 1:2, and so on. Furthermore, with respect to the alloyed semiconductor quantum dots of the series, at least one of the alloyed semiconductor quantum dots of the series is characterized by a band gap energy that is non-linearly related to the molar ratio of the at least two semiconductors.

The present invention also provides a series of concentration-gradient quantum dots. Each quantum dot of the series comprises an alloy of a first semiconductor and a second semiconductor. For each quantum dot, the concentration of the first semiconductor gradually increases from the core of the quantum dot to the surface of the quantum dot and the concentration of the second semiconductor gradually decreases from the core of the quantum dot to the surface of the quantum dot. In this manner, a two-way concentration-gradient is established along the radius of the quantum dot. With respect to the concentration-gradient quantum dots of the present inventive series, the gradient by which the concentration of the first semiconductor increases and the gradient by which the concentration of the second semiconductor decreases from the core of the quantum dot to the surface of the quantum dot varies among the quantum dots of the series. In other words, the point along the radius of the quantum dot at which the molar ratio of the first semiconductor to the second semiconductor is 1:1 differs for each concentration-gradient quantum dot within the series. Like the series of alloyed semiconductor quantum dots, the size of each quantum dot of the series of concentration-gradient quantum dots is within about 5% of the size of the average-sized quantum dot and each concentration-gradient quantum dot comprises the same semiconductors.

With respect to the present inventive series of quantum dots described herein, one of ordinary skill in the art realizes that the limitations and descriptions that apply to the present inventive individual quantum dots disclosed herein can also apply to the quantum dots of the present inventive series.

Methods of Using the Quantum Dots

The present inventive quantum dots are useful in a number of in vitro and in vivo methods, particularly, in the instance that the quantum dots are conjugated to a biological agent, such as a biomolecule or any drug. As used herein, the term "in vitro" means that the method does not take place within a host. As used herein, the term "in vivo" means that the method takes place within a host or any part thereof. These methods are further provided by the present invention.

In this regard, the present invention provides a method of detecting a target in a sample. The method comprises (i) contacting a sample with an alloyed semiconductor quantum dot or a concentration-gradient quantum dot, either of which is conjugated to a biological agent, wherein the biological agent specifically binds to a target in the sample, (ii) allowing the biological agent to specifically bind to the target, and (iii) analyzing the sample via spectroscopy, thereby obtaining a spectroscopic signature of the sample, wherein the spectroscopic signature is indicative of the presence or the absence of the target in the sample.

The present invention also provides a method of detecting the location of a target within a sample. The method comprises (i) contacting a sample with an alloyed semiconductor quantum dot or a concentration-gradient quantum dot, either of which is conjugated to a biological agent, wherein the biological agent specifically binds to a target in the sample, (ii) allowing the biological agent to specifically bind to the target, and (iii) imaging the sample or a section thereof, thereby detecting the location of the target within the sample.

Also provided by the present invention is a method of monitoring a biological process in vitro. The method comprises (i) contacting a sample with an alloyed semiconductor quantum dot or a concentration-gradient quantum dot, either of which is conjugated to a biological agent, wherein the biological agent specifically binds to a target in the sample, wherein the target functions in a biological process, (ii) allowing the biological agent to specifically bind to the target, and (iii) imaging the sample or a section thereof over a period of time or before and after a stimulus, thereby monitoring a biological process in vitro.

The present invention provides a method of detecting the location of a target in vivo. The method comprises (i) administering to a host an alloyed semiconductor quantum dot or a concentration-gradient quantum dot, either of which is conjugated to a biological agent, wherein the biological agent specifically binds to a target in the host, (ii) allowing the biological agent to specifically bind to the target, (iii) imaging the host, a section thereof, or a cell thereof, thereby detecting the location of the target in vivo.

The present invention provides a method of monitoring a biological process in vivo. The method comprises (i) administering to a host an alloyed semiconductor quantum dot or a concentration-gradient quantum dot, either of which is conjugated to a biological agent, wherein the biological agent specifically binds to a target in the host, wherein the target functions in a biological process, (ii) allowing the biological agent to specifically bind to the target, and (iii) imaging the host, a section, or a cell thereof over a period of time or before and after a stimulus, thereby monitoring a biological process in vivo.

Likewise, the present inventive series of quantum dots are useful in a number of in vitro and in vivo methods, especially in the case that each of the quantum dots of the series is conjugated to a different biological agent, such that each of the different biological agents corresponds to a quantum dot having a unique molar ratio of the at least two semiconductors. One of ordinary skill in the are appreciates that use of any of the present inventive series of quantum dots can provide simultaneous detection or monitoring of more than one target.

In this regard, the present invention also provides a method of detecting more than one target in a sample. The method comprises (i) contacting a sample with a series of alloyed semiconductor quantum dots or a series of concentration-gradient quantum dots, wherein each of the quantum dots of either series is conjugated to a different biological agent, wherein each of the biological agents specifically bind to a different target in the sample, (ii) allowing the biological agents to specifically bind to the targets, and (iii) analyzing the sample via spectroscopy, thereby obtaining a spectroscopic signature of the sample, wherein the spectroscopic signature is indicative of the presence or absence of the more than one target in the sample, thereby detecting more than one target in a sample.

The present invention also provides a method of detecting the location of more than one target within a sample. The method comprises (i) contacting a sample with a series of alloyed semiconductor quantum dots or a series of concentration-gradient quantum dots, wherein each of the quantum dots of either series is conjugated to a different biological agent, wherein each of the biological agents specifically binds to a different target in the sample, (ii) allowing the biological agents to specifically bind to the targets, (iii) imaging the sample or a section thereof, thereby detecting the location of the more than one target within the sample.

Further provided by the present invention is a method of monitoring a biological process in vitro. The method comprises (i) contacting a sample with a series of alloyed semiconductor quantum dots or a series of concentration-gradient quantum dots, wherein each of the quantum dots of either series is conjugated to a different biological agent, wherein each of the biological agents specifically binds to a different target in the sample, wherein each of the targets functions in a biological process, (ii) allowing the biological agents to specifically bind to the targets, and (iii) imaging the sample or a section thereof over a period of time or before and after a stimulus, thereby monitoring a biological process in vitro.

A method of detecting the location of more than one target in vivo is provided by the present invention. The method comprises (i) administering to a host a series of alloyed semiconductor quantum dots or a series of concentration-gradient quantum dots, wherein each of the quantum dots of either series is conjugated to a different biological agent, wherein each of the biological agents specifically binds to a different target in the host, (ii) allowing the biological agents to specifically bind to the targets, (iii) imaging the host, a section thereof, or a cell thereof, thereby detecting the location of the more than one target in vivo.

The present invention also provides a method of monitoring a biological process in vivo. The method comprises (i) administering to a host a series of alloyed semiconductor quantum dots or a series of concentration-gradient quantum dots, wherein each of the quantum dots of either series is conjugated to a different biological agent, wherein each of the biological agents specifically binds to a different target in the host, wherein each of the targets functions in a biological process, (ii) allowing the biological agents to specifically bind to the targets, and (iii) imaging the host, a sample thereof, or a section thereof over a period of time or before and after a stimulus, thereby monitoring a biological process in vivo.

As used herein, the term "target" refers to any entity that specifically binds to a biological agent conjugated to a quantum dot. The target can be, for instance, a protein, a nucleic acid molecule, a fragment of either of the foregoing, a small-molecule drug, a cell, a tissue, or a drug metabolite. Suitable targets that are proteins include, but are not limited to, antibodies, or fragments thereof, peptides, hormones, growth factors, cytokines, tumor-associated proteins, cell-surface receptors, coagulation factors, proteins associated with a disease or a condition, and the like. One of ordinary skill in the art realizes that the phrase "specifically binds to" generally means that the binding occurs in such a manner that excludes the binding of most other entities within the sample or host. A target-biological agent binding interaction typically has a dissociation constant, KD, within the range of about micromolars to about picomolars. The phrase "allowing the biological agent to specifically bind to the target" as used herein refers to providing conditions under which the biological agent will specifically bind to the target. Such conditions are empirically determined by one of ordinary skill in the art by varying certain parameters, e.g., salt concentrations, pH, temperature, concentration of the target, concentration of the biological agent. One ordinarily skilled appreciates that these parameters affect the specific binding of the biological agent to the target. Typically, but not always, suitable conditions for allowing the biological agent to specifically bind to the target are physiological conditions, such that in the in vivo methods described herein, suitable conditions may be providing a sufficient period of time for the biological agent to specifically bind to the target.

With respect to the present inventive in vitro methods, i.e., the method of detecting a target in a sample, the method of detecting more than one target in a sample, and the method of monitoring a biological process in vitro, the sample can be any sample, such as blood, lymph, ductal fluid, tissue, cell cultures, a single cell, urine, a biopsy, and the like. The sample can also be obtained from any source, such as a host, an animal, a cultured cell line, a plant, and a tumor. The terms "host" and "whole organism" as used herein refers to any living organism, including for example, bacteria, yeast, fungi, plants, and mammals. Preferably, the host is a mammal. For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In one embodiment of the invention, the source can represent a normal, undiseased state. Alternatively, the source, such as the mammal, has a disease or a condition, such that the method achieves detection or prognosis of the disease or the condition. In a preferred embodiment of the invention, the disease is cancer including, but not limited to, lung cancer, brain cancer, ovarian cancer, uterine cancer, testicular cancer, lymphoma, leukemia, stomach cancer, pancreatic cancer, skin cancer, breast cancer, adenocarcinoma, glioma, bone cancer, and the like. The present inventive methods of detecting cancer are particularly useful for detecting skin and breast tumors that are located close to the skin surface.

In some of the present inventive in vitro methods described herein, the sample is analyzed via spectroscopy in order to obtain a spectroscopic signature. By "spectroscopy" as used herein is meant any technique for analyzing molecules based on how they absorb radiation. One of ordinary skill in the art realizes that many methods of spectroscopy are known in the art, including, for instance, ultraviolet-visible (UV-VIS) spectroscopy, infrared (IR) spectroscopy, fluorescence spectroscopy, Raman spectroscopy, mass spectrometry, and nuclear magnetic resonance (NMR). For the present inventive methods, the sample preferably is analyzed via fluorescence spectroscopy. More preferably, the sample is analyzed via visible to infrared fluorescence spectroscopy and, most preferably, the sample is analyzed via far-red and near-infrared fluorescence. The term "spectroscopic signature" as used herein refers to a resulting pattern, plot, or spectrum obtained upon performing spectroscopy on a sample. The spectroscopic signature obtained of a sample containing a biological agent bound to a target can be compared to a control spectroscopic signature, wherein the target is not present in the sample or host.

With respect to the present inventive methods of detecting a location of a target or detecting locations of more than one target, the term "location" as used herein refers to the physical position or site where the target is found within the sample or host. The location can be in reference to a cell, i.e., a subcellular location. Alternatively, the location of the target can be in reference to a tissue or an organ. The location of the target can also be in, reference to a whole organism, a whole plant or whole animal. The location can be on the surface of the host or animal or it can be within the host or animal. Preferably, the location of the target is deep within the animal or host, i.e., underneath several layers of tissue.

The location of the target is determined via imaging the sample with the conjugated quantum dot bound to the target. Many methods of imaging are known in the art, including, for example, x-ray computed tomography (CT), magnetic resonance imaging (MRI), positron emission tomography (PET), and optical imaging. Preferably, the imaging is done via fluorescence. More preferably, the imaging is done via visible to infrared fluorescence and, most preferably, the imaging is done through far-red and near-infrared fluorescence. One of ordinary skill in the art realizes that most, if not all, forms of imaging involve the detection of the wavelengths emitted by the quantum dot(s). The present inventive quantum dots having the unique optical properties as discussed herein can have an emission peak wavelength that is within the near infrared spectrum or far red spectrum. In this regard, methods requiring imaging of the present inventive quantum dots can involve detection of near infrared or far red emission peak wavelengths. One ordinarily skilled also appreciates that this property of the quantum dots allow imaging of targets deep within a host or animal.

The term "biological process" as used herein refers to any event, physiological or molecular, that occurs in or on the body of a host. The biological process can be, for instance, a molecular process (e.g., signal transduction pathway, a chemical reaction, an enzyme reaction, a binding reaction), a cellular process (e.g., mitosis, cytokinesis, cell motility, cell proliferation, cellular differentiation, cell lysis, endocytosis, phagocytosis, exocytosis, cell fusion), a physiological process (e.g., blood clot formation), and the like. The biological process can be one that occurs in response to a stimulus or the process can be one that occurs without stimulus and takes place over a period of time. A stimulus can be exogeneous (not naturally-occurring) or endogeneous (naturally-occurring) to the whole organism. The stimulus can vary in duration. It can be incessant or it can be a short event that occurs only once. It can also be a short, repeated stimulus. Suitable stimuli for use in the present inventive methods include, but are not limited to, an injection of a drug or a hormone, exposure to light, pain, electrical pulses, magnetic fields, temperature, and the like.

The quantum dots described herein can be formed as a composition, such as a pharmaceutical composition. Pharmaceutical compositions containing the quantum dots can comprise more than one active ingredient, such as more than one quantum dot conjugated to a different biological agent. The pharmaceutical composition can alternatively comprise a quantum dot in combination with pharmaceutically active agents or drugs other than those conjugated to them.

The compositions comprising the quantum dots can comprise a carrier, a diluent, or an excipient. The carrier can be any suitable carrier. Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. It will be appreciated by one of skill in the art that, in addition to the following described pharmaceutical composition, the quantum dots of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular quantum dot and biological agent conjugated thereto, as well as by the particular method used to administer the compound and/or inhibitor. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the quantum dots of the present invention are known, and, although more than one route can be used to administer a particular quantum dot, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations are well-known to those of skill in the art. Such formulations are particularly suitable in the context of the present invention for application to the skin.

Formulations suitable for oral administration can consist of (a) liquid solutions, such as an effective amount of the quantum dot dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The quantum dots, alone or in combination with each other and/or with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The quantum dots can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5% to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the quantum dots, or compositions comprising such compounds and/or inhibitors of Hsp90, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

One of ordinary skill in the art will readily appreciate that the quantum dots of the present inventive methods can be modified in any number of ways, such that the efficacy of the quantum dot is increased through the modification. For instance, the quantum dot or the biological agent conjugated thereto could be conjugated either directly or indirectly through a linker to a targeting moiety. The practice of conjugating quantum dots or biological agents to targeting moieties is known in the art. See, for instance, Wadwa et al., *J. Drug Targeting* 3: 111 (1995), and U.S. Pat. No. 5,087,616. The term "targeting moiety" as used herein, refers to any molecule or agent that specifically recognizes and binds to a cell-surface receptor, such that the targeting moiety directs the delivery of the quantum dot and/or biological agent to a population of cells on which surface the receptor is expressed. Targeting moieties include, but are not limited to, antibodies, or fragments thereof, peptides, hormones, growth factors, cytokines, and any other naturally- or non-naturally-existing ligands, which bind to cell surface receptors. The term "linker" as used herein, refers to any agent or molecule that bridges the quantum dot or biological agent to the targeting moiety. One of ordinary skill in the art recognizes that sites on the quantum dot or biological agent, which are not necessary for the function of the quantum dot or biological agent, are ideal sites for attaching a linker and/or a targeting moiety, provided that the linker and/or targeting moiety, once attached to the quantum dot or biological agent, do(es) not interfere with the function of the quantum dot or biological agent, i.e., the ability to absorb and emit detectable energy or specifically bind to a target or targets.

Alternatively, the quantum dots of the present invention can be modified into a depot form, such that the manner in which the quantum dot is released into the body to which it is administered is controlled with respect to time and location within the body (see, for example, U.S. Pat. No. 4,450,150). Depot forms of quantum dots can be, for example, an implantable composition comprising the quantum dot and a porous material, such as a polymer, wherein the quantum dot is encapsulated by or diffused throughout the porous material. The depot is then implanted into the desired location within the body and the quantum dot is released from the implant at a predetermined rate by diffusing through the porous material.

Furthermore, the present inventive methods can comprise the administration of the quantum dot(s), in the presence or absence of an agent that enhances its efficacy, or the methods can further comprise the administration of other suitable components, such as those that can protect the quantum dot and/or the biological agent from degradation within the host or those that can prevent the elimination from the host or cellular uptake of the quantum dot.

For purposes of the present inventive methods, the amount or dose of the quantum dot(s) administered should be sufficient to effect a response in the animal over a reasonable time frame. Particularly, the dose of the quantum dot should be sufficient to allow the biological agent(s) to specifically bind to its target(s) within about 1-2 hours, if not 3-4 hours, from the time of administration. The dose will be determined by the efficacy of the particular quantum dot and/or biological agent conjugated thereto and the condition of the animal (e.g., human), as well as the body weight of the animal (e.g., human) to be treated. Many assays for determining an administered dose are known in the art. For purposes of the present invention, an assay, which comprises comparing the extent to which the biological agent(s) specifically bind(s) to its target(s) within the host upon administration of a given dose of a quantum dot to a mammal among a set of mammals that are each given a different dose of the quantum dot(s), could be used to determine a starting dose to be administered to a mammal. The extent to which the biological agent conjugated to the quantum dot specifically binds to the target within the host upon administration of a certain dose can be determined through imaging the host or a section thereof.

The dose also will be determined by the existence, nature and extent of any adverse side effects that might accompany the administration of a particular quantum dot. Ultimately, the attending physician will decide the dosage of the compound or inhibitor of the present invention with which to treat each individual patient, taking into consideration a variety of factors, such as age, body weight, general health, diet, sex, quantum dot to be administered, and route of administration.

In addition to the present inventive methods of using the quantum dots or series comprising the quantum dots described herein, the quantum dots can be used in optoelectronic methods or as optoelectronic devices. For instance, the quantum dots can be used as light emitting diodes or as solar cells. See, for instance, Huynh, et al., *Advanced Functional Materials*, 13: 73-79 (2003), Milliron, et al., *Advanced Materials*, 15: 58-61 (2003), Schlamp, et al., *Journal of Applied Physics*, 82, 5837-5842 (1997). The quantum dots can be used in lieu of bulk materials when the bulk materials with the desired electronic properties are not available. In this instance, the quantum dots would be arranged and deposited onto a substrate. For example, in an array as a thin film or layers of thin films on a support substrate or as a coating on or around another electronic material. Subsequently the support substrate and layered quantum dot film or other coated electronic material can be processed as needed in similar fashion to bulk semiconductor materials with the unique properties of the quantum dots now available for use in electronic and optoelectronic devices.

Methods of Producing Quantum Dots

The present invention further provides methods of producing the quantum dots of the present invention and methods of producing the series comprising the quantum dots of the present invention. In this respect, the present invention also provides a method of producing a quantum dot comprising an alloy of at least two semiconductors. The method comprises (i) providing a first solution under conditions which allow nanocrystal formation to take place, (ii) providing a second solution comprising precursors of the at least two semiconductors at a molar ratio under conditions which do not allow nanocrystal formation to take place, (iii) adding the second solution to the first solution, thereby allowing nanocrystal formation to take place, and (iv) changing the conditions to conditions that halt nanocrystal growth and formation. Upon this method, a quantum dot comprising an alloy of at least two semiconductors is produced.

Further provided by the present invention is a method of producing a ternary alloyed semiconductor quantum dot comprising an alloy of two semiconductors AB and AC, wherein A is a species that is common to the two semiconductors and B and C are each a species that is found in one of the two semiconductors. The method comprises (i) providing a first solution under conditions which allow nanocrystal formation to take place, (ii) providing a second solution comprising A, B, and C under conditions which do not allow nanocrystal formation to take place, wherein A is present in the second solution at concentration that is reaction-limiting, (iii) adding the second solution to the first solution, thereby allowing nanocrystal formation to take place, (iv) changing the conditions to conditions that halt nanocrystal growth and formation.

The present invention also provides a method of producing a series of ternary alloyed semiconductor quantum dots, wherein each quantum dot comprises an alloy of two semiconductors AB and AC, wherein A is a species that is common to the two semiconductors and B and C are each a species that is found in one of the two semiconductors The method comprises (i) providing a first solution under conditions which allow nanocrystal formation to take place, (ii) providing a second solution comprising A, B, and C at a molar ratio under conditions which do not allow nanocrystal formation to take place, wherein A is present in the second solution at concentration that is reaction-limiting, (iii) adding the second solution to the first solution, thereby allowing nanocrystal formation to take place, (iv) changing the conditions to conditions that halt nanocrystal growth and formation, and (v) repeating steps (i)-(iv) at least one time, thereby producing at least one other quantum dot in the series, wherein each time the molar ratio of A, B, and C is different from the molar ratio of A, B, and C of the other quantum dots of the series.

A method of producing a ternary concentration-gradient quantum dot comprising a first semiconductor AB and a second semiconductor AC, wherein A is a species that is common to the first semiconductor and the second semiconductor and B and C are each a species found in only one of the first semiconductor and the second semiconductor, is also provided by the present invention. The method comprises (i) providing a first solution under conditions which allow nanocrystal formation to take place, (ii) providing a second solution comprising A, B, and C at a molar ratio under conditions which do not allow nanocrystal formation to take place, wherein each of B and C are present in the second solution at a concentration that is reaction-limiting, (iii) adding the second solution to the first solution, thereby allowing nanocrystal formation to take place, and (iv) changing the conditions to conditions that halt nanocrystal growth and formation.

The present invention provides a method of producing a series of ternary concentration-gradient quantum dots, wherein each of the quantum dots comprise a first semiconductor AB and a second semiconductor AC, wherein A is a species that is common to the first semiconductor and the second semiconductor and B and C are each a species found in only one of the first semiconductor and the second semiconductor. The method comprises (i) providing a first solution under conditions which allow nanocrystal formation to take place, (ii) providing a second solution comprising A, B, and C at a molar ratio under conditions which do not allow nanocrystal formation to take place, wherein each of B and C are present in the second solution at a concentration that is reaction-limiting, (iii) adding the second solution to the first solution, thereby allowing nanocrystal formation to take place, (iv) changing the conditions to conditions that halt nanocrystal growth and formation, and (v) repeating steps (i)-(iv) at least one time, thereby producing at least one other quantum dot of the series, wherein each time the molar ratio of A, B, and C is different from the molar ratio of A, B, and C of the other quantum dots of the series.

With respect to the present inventive methods of producing quantum dots, the phrase "conditions which allow nanocrystal formation" as used herein refers to the environment within which a quantum dot (nanocrystal) forms. Suitable conditions for quantum dot (nanocrystal) formation can be empirically determined by one of ordinary skill in the art, who realizes that the conditions depend, in part, on the semiconductors comprising the quantum dot(s). In the case that the quantum dot comprises the two semiconductors CdSe and CdTe, suitable conditions are suitable conditions are achieved by combining the precursors and introducing them into a hot (greater than 200° C.) solvent such as tri-n-octylphosphine oxide with vigorous stirring. See Example 1 for more description of the conditions that allow nanocrystal formation to take place. The phrase "conditions which halt nanocrystal growth and formation" as used herein means the environment within which a quantum dot (nanocrystal) does not form and previously formed nanocrystals stop growing. Suitable conditions under which a quantum dot (nanocrystal) does not form can also be empirically determined by one of ordinary skill in the art, who realizes that the conditions depend, in part, on the semiconductors comprising the quantum dot(s). In the case that the quantum dot comprises the two semiconductors CdSe and CdTe, suitable conditions are suitable conditions are achieved when the solvent temperature is lowered sufficiently such that nanocrystal growth and formation are negligible (typically a temperature less than 200° C. and ideally a temperature less than 100° C.). See Example 1 for more description of the conditions that halt nanocrystal growth and formation.

The term "precursors" as used herein refers to the elements of the semiconductors in either an elemental form or as part of a compound. For instance, the precursors of the two semiconductors CdSe and CdTe are Cd, Se, and Te. In the methods of producing a quantum dot comprising these semiconductors, Se and Te are typically in the second solution in their elemental states, whereas, Cd is generally provided in the second solution as a compound, either, cadmium oxide or dimethyl cadmium.

The phrases "species that is common" and "species that is found in one of the two semiconductors" is best explained by way of example. For instance, for the two semiconductors CdSe and CdTe, the species that is common is Cd, while the species that is found in one of the two semiconductors is both Se and Te.

The phrase "a concentration that is reaction-limiting" as used herein refers to a concentration that limits the reaction, wherein the reaction is the formation of the quantum dot (nanocrystal). Reaction-limiting concentrations can be empirically determined by one of ordinary skill in the art. Without being held to any particular theory, the quantum dot produced by the method will be either an alloyed semiconductor quantum dot or a concentration-gradient quantum dot depending on which precursor(s) are present in the second solution at a reaction-limiting concentration. If the precursor is the species that is common to the two semiconductors, then an alloyed semiconductor quantum dot is produced. If the precursors are the species that are each found in only one of the two semiconductors, then a concentration-gradient quantum dot is produced.

In the present inventive methods of producing a series of quantum dots, the first four steps, which yield a single quantum dot, are repeated at least one time, thereby producing at least one other quantum dot. Preferably, the steps are repeated several times, such that several quantum dots are produced. One ordinarily skilled understands that each time the steps are repeated, the precursors of the semiconductors will be present in the second solution at a molar ratio that is different from the previous times, such that each quantum dot produced will have a unique molar ratio. Also, it is understood by one of ordinary skill in the art that the quantum dots are generally produced by batch, such that several copies of the same quantum dot having a specific molar ratio are produced.

The following examples further illustrate the invention but, of course, should not be construed as in any way limiting its scope.

EXAMPLES

Abbreviations

For convenience, the following abbreviations have been used herein:

CdO, cadmium oxide; TOPO, tri-n-octylphosphine oxide; HDA, hexadecylamine, TOP, tri-n-octylphosphine; TEM, transmission electron microscopy; PL, photoluminescence; QDs, quantum dots; CCD, charge coupled device; x, any fractional number between 0 and 1.

Materials

Cadmium oxide (CdO, 99.99%), selenium shot (Se, 99.999%), bis(trimethylsilyl) sulfide ($C_6H_{18}SSi_2$), tri-n-octylphosphine ($C_{24}H_{51}P$ or TOP, 90%), tri-n-octylphosphine oxide ($C_{24}H_{51}PO$ or TOPO, 90%) and hexadecylamine ($C_{16}H_{35}N$ or HDA, 90%) were purchased from Aldrich (Milwaukee, Wis.). Tellurium powder (Te, 99.999%) was purchased from Alfa Aesar (Ward Hill, Mass.). Dimethyl cadmium ($C_2H_6Cd$, 97%) was obtained from Strem (Newburyport, Mass.). Reference organic dyes, Atto 565 and Atto 680, were purchased from Fluka (St Louis, Mo.). All other solvents used where purchased from Aldrich. Carbon-coated copper grids (200 mesh) for preparing transmission electron microscopy (TEM) specimens were purchased from Electron Microscopy Sciences (Fort Washington, Pa.). All materials were used as received from the supplier.

Stock solutions were prepared and stored under nitrogen in a dry box at room temperature, unless otherwise noted. A 0.4 M selenium stock solution was prepared by dissolving 0.79 g of selenium shot in 25 mL of TOP, yielding a colorless solution. Likewise, a 0.4 M Te stock solution was prepared by dissolving 1.28 g of tellurium powder in 25 ml, of TOP, yielding a yellow saturated solution which required gentle heating before use in order to dissolve the remaining tellurium powder. A 0.1 M CdS stock solution was prepared by dissolving 0.18 mL of dimethyl cadmium and 0.53 mL bis (trimethylsilyl) sulfide in 25 mL of TOP and was stored under argon and refrigerated.

Example 1

This example demonstrates a method of producing a series of alloyed semiconductor quantum dots.

All manipulations were carried out under argon on a schlenk line using standard airless techniques (Jolly, *The Synthesis and Characterization of Inorganic Compounds*, Waveland Press (1991)). A 125 mL roundbottom flask equipped with a stop-cocked sidearm was charged with 9 g TOPO, 3 g HDA and 50 mg CdO and fitted with a septum. The flask was placed in a heating mantle and evacuated on the schlenk line. The flask was heated to 150° C. and degassed under a vacuum of 20 Pa for 15 minutes. At this point, the flask filled with argon and the temperature increased to 325° C. After the CdO was completely dissolved, the temperature was lowered to 300° C. and allowed to stabilize for several minutes. To achieve an 2-fold excess of cadmium precursor with respect to the total chalcogenide used, a syringe was charged with 0.5 ml of a premixed Se and Te stock solution containing selenium and tellurium in a given ratio, i.e., 100:0, 75:25, 50:50, 25:75, or 0:100. This maintained a total chalcogen concentration of 0.4 M but varied the relative amounts of Se and Te from 100% Se to 100% Te. This solution was rapidly injected (less than 1 s) into the colorless TOPO/HDA solution containing the cadmium precursor at 300° C. Immediately, the solution changed from colorless to a deeply colored solution, the exact color of which depended on the composition of the stock solution. The growth period required to obtain the desired nanocrystal size at a given composition was determined empirically after observing the growth rates of several trials. After the correct growth time elapsed, the reaction mixture was quenched in cold (25° C.) chloroform to stop any further growth of the particles.

Example 2

This example demonstrates a study of the role of cadmium surface sites on colloidal stability.

For experiments designed to study the role of cadmium surface sites on colloidal stability, the previously described synthesis was utilized with the only change that the quantity of cadmium precursor added was adjusted to achieve the desired cadmium:chalcogen ratio. Water-soluble quantum dots (QDs) were prepared as outlined by Chan et al. (Chan et al., *Science* 281: 2016-2018 (1998)) using mercaptoacetic acid as the surface molecule.

Example 3

This example demonstrates the synthesis of alloyed semiconductor quantum dots encapsulated in a semiconductor shell.

Nanocrystal cores of $CdSe_{1-x}Te_x$ were obtained by using the procedure outlined in the previous section. These nanocrystals were isolated by precipitation with methanol followed by centrifugation and placed into a 125 mL roundbottom flask equipped with a stop-cocked sidearm containing 12 g of TOPO. This vessel was placed in a heating mantle and evacuated on the schlenk line. The flask was then heated to 75° C.

and degassed under a vacuum of 20 Pa for 15 minutes. At this point, the flask filled with argon and the temperature increased to 200° C. Shells were grown epitaxially by dropwise addition of the CdS stock solution. The optimal shell thickness was determined by periodically taking aliquots from the reaction mixture and observing the intensity of the PL peak while the CdS stock solution was added. The addition of CdS stock solution was stopped at the first indication of attenuation of the PL emission intensity. The CdS-capped $CdSe_{1-x}Te_x$ nanocrystals were isolated from the raw reaction mixture by precipitating with methanol, centrifugation, decanting the supernate and redispersing in chloroform for storage.

Example 4

This example demonstrates the characterization of the alloyed semiconductor quantum dots.

Photoluminescence spectra were acquired on a Spex FluoroMax-2 spectrometer. Emission spectra were taken using an excitation wavelength of 475 nm with excitation and emission slit widths set at 2.0 nm. Recorded spectra were corrected for the wavelength-dependent detector response. The optical density of all samples was adjusted to between 0.10 and 0.15 at the excitation wavelength and quantum yield measurements were made by comparing the integrated nanocrystal emission in chloroform and water with that of reference organic dyes in ethanol and water. Absorption spectra were recorded on a Shimadzu UV-2401PC scanning spectrophotometer operating at a slit width of 1.0 nm. Transmission electron micrographs were obtained at the on a Philips CM200 electron microscope operating at an accelerating voltage of 120 kV. Samples were prepared by placing 5 μL of a dilute solution of nanocrystals in chloroform onto carbon-coated copper grids and allowing them to dry in a vacuum dessicator overnight.

Powder samples of $CdSe_{1-x}Te_x$ nanocrystals were obtained by precipitating nanocrystals in chloroform with methanol followed by centrifugation to isolate a nanocrystal pellet. Discarding the supernatant, each pellet was allowed to dry overnight and then crushed into a fine powder, which was sealed in a 0.5 mm capillary and mounted on the platform goniometer such that the capillary axis was coincident with the main instrument axis. Data were collected using Mo Kα radiation with a weighted mean wavelength of 0.71073 Å. The samples were continuously oscillated through 179 degrees about the instrument axis during a ninety-second data collection period. Data were recorded with a Bruker-AXS SMART 6000 two-dimensional CCD detector diffraction system and processed with Bruker's SMART and GADDS software to produce the standard intensity vs. diffraction angle data to a maximum diffraction angle, 2θ, of 39.5°. The data were further processed by using the PowderX software program to perform background reduction. Elemental analysis was carried out on a LECO Renaissance inductively couple plasma/time-of-flight mass spectrometer. Aqueous quantum dot colloids treated with dilute acid were introduced into the atomization chamber and carried to the inductively couple plasma torch by a flow of argon buffer gas. Mass spectra where recorded and elemental abundances where calculated by comparison with calibrated standard data.

Figure 2:
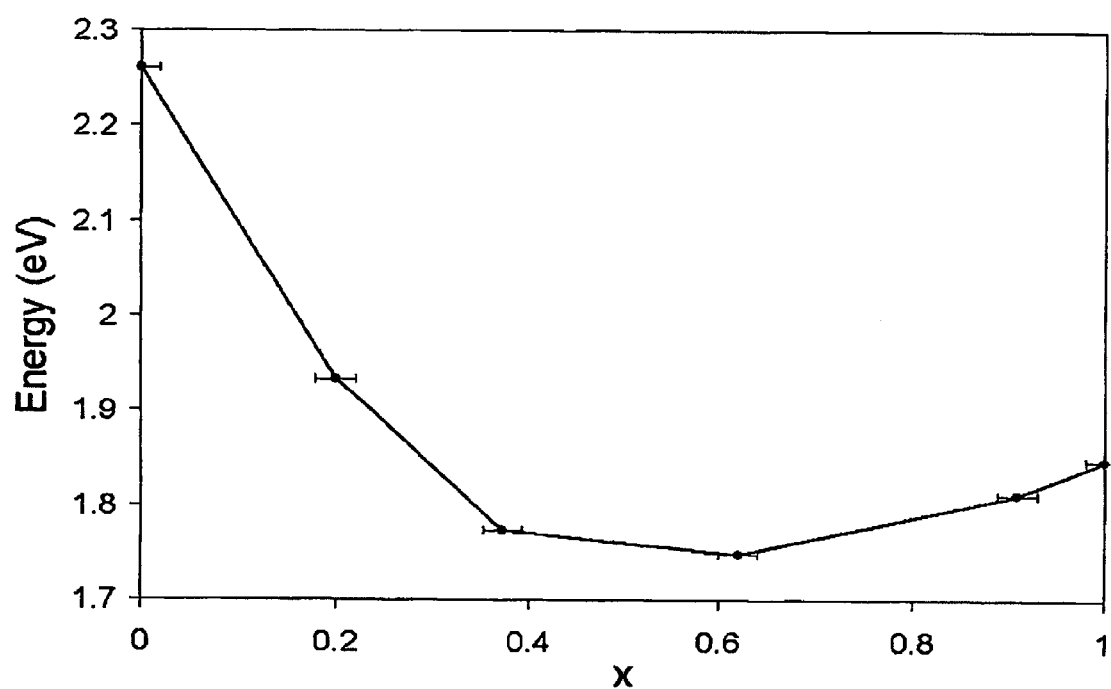
FIG. 2: Plot of the average emission energy as a function of composition for 2.9±0.3 nm (mean diameter) $CdSe_{1-x}Te_x$ nanocrystals. The uncertainty in the composition determination is ±0.02 units as indicated by error bars.

Ternary nanocrystals were synthesized by injecting a premixed stock solution containing selenium and tellurium in a given ratio into a coordinating solvent that contained a previously dissolved cadmium precursor. In order to maintain a fixed size throughout the composition range (x=0 to x=1), the strategies of Alivisatos and coworkers were used for size control and focusing (Peng et al., *J. Am. Chem. Soc.* 120: 5343-5344 (1998)). This was achieved by carefully controlling the concentrations of the reagents and the growth time. FIG. 1 shows the photoluminescence spectra for a series of $CdSe_{1-x}Te_x$ nanocrystals with a mean diameter of 2.9±0.3 nm. At this particular size, the emission wavelength of pure CdSe nanocrystals is 547 nm, while that of pure CdTe nanocrystals is 672 nm. For the ternary nanocrystals, the emission wavelengths are considerably longer than those of the binary nanocrystals when the mole fraction of tellurium is between 0.35 and 0.90. With the longest emission wavelength at 712 nm and the shortest wavelength at 547 nm, the emission maximum can be tuned continuously from one extreme to the other by controlling the mole ratio of the injected stock solution without changing the actual size of the particle. To further examine how composition modulates the emission wavelength, the PL energy as function of tellurium content (FIG. 2) is plotted. The curve reveals a strong nonlinear dependence and shows that the lowest emission energy (longest wavelength) occurs for nanocrystals whose composition corresponds to a mole fraction of approximately 0.62 in tellurium.

Figure 3:
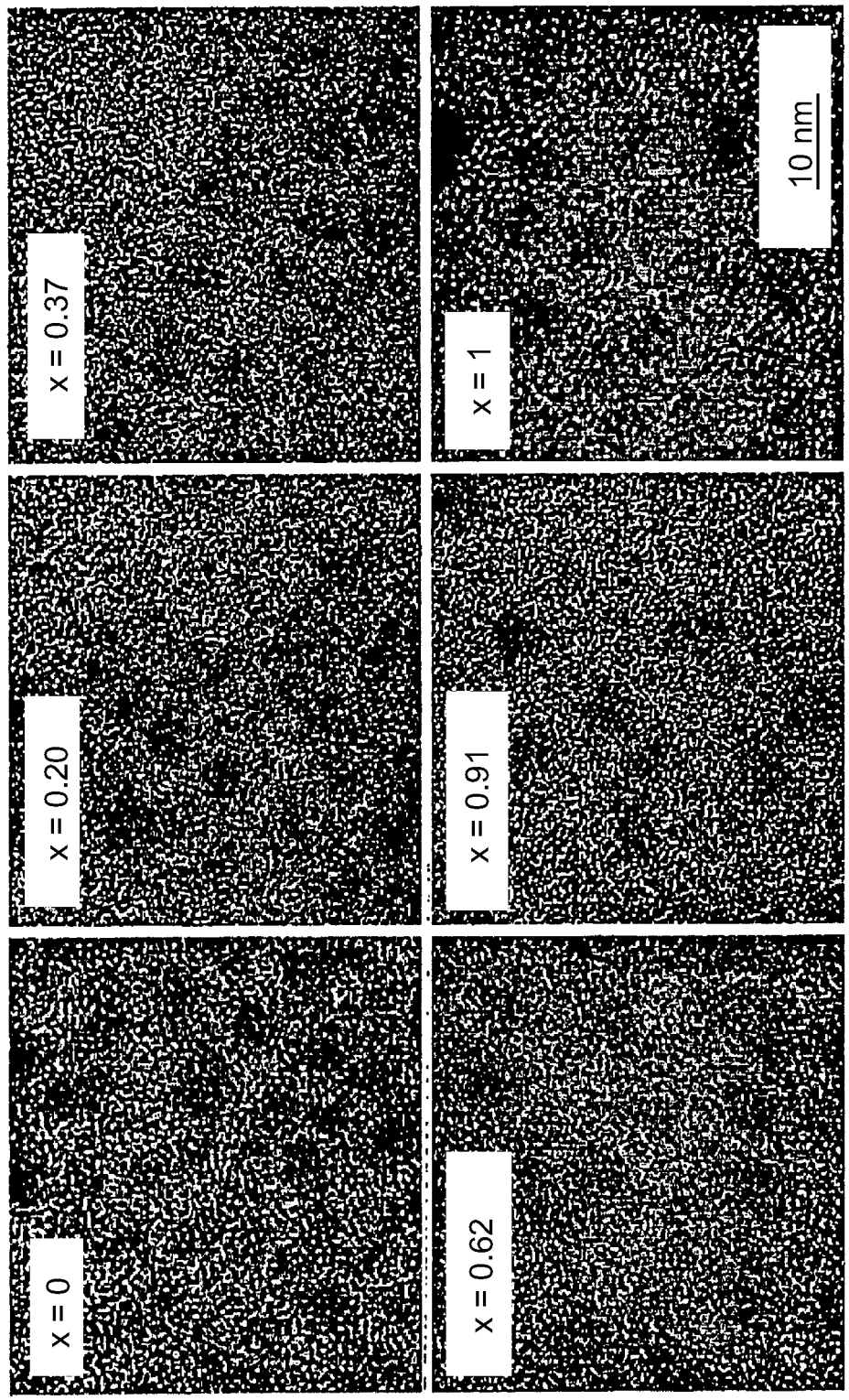
FIG. 3: Transmission electron micrographs of $CdSe_{1-x}Te_x$ nanocrystals at various compositions as indicated. The synthesis of each sample in the series was carried out as to insure a mean particle size as close as possible to 3 nm.

To confirm that the particle size is constant throughout the sample series, transmission electron microscopy (TEM) images of the nanocrystals (FIG. 3) were obtained. Statistical analysis of the TEM data indicates a constant particle size of 2.9±0.3 nm (mean diameter). Powder X-ray diffraction patterns further reveal that the particles are highly crystalline and that the wurtzite structure is favored for all compositions under our rapid-growth conditions. In addition, elemental analysis was carried out by using inductively-coupled plasma mass spectrometry, which revealed that the nanocrystal composition was skewed toward tellurium in comparison with the Se:Te mole ratio in the stock solution. This composition bias is due to the fact that tellurium has a higher reactivity than selenium towards cadmium.

It is important to note the particle size variations and measurement errors are not large enough to account for the nonlinear relationship, indicating that the observed wavelength changes are caused by a composition effect. In this particular system, there are two distinct sources which contribute to this composition dependence. The first arises from the phenomenon that can be observed in the bulk material, where the band-gap energy changes as the alloy composition is varied (Willardson et al., *Compound Semiconductors*, Reinhold, New York, (1962)). The other can be traced to the quantum-confined nature of this nanocrystalline system. Recently, Poon et al. examined the composition-dependent optical properties of bulk $CdSe_{1-x}Te_x$ (Poon et al., *J. Phys.: Condensed Matter* 7: 2783-2799 (1995)). They noted that this particular material exhibits a much greater nonlinear effect than other members of the mixed chalcogenide semiconductor family. In a model developed by Bernard and Zunger (Bernard et al., *Phys. Rev. B* 36: 3199-3226 (1987)), three factors are believed to contribute to the observed nonlinear dependence: (i) a volume deformation which arises from the variation in the lattice constant of the changing alloy composition, (ii) a chemical-electronegativity effect, and (iii) internal relaxation of the anion-cation bond lengths in the alloy. This model has been used to explain the composition-dependent properties of bulk $CdSe_{1-x}Te_x$ with reasonable success (Poon et al., *J. Phys.: Condensed Matter* 7: 2783-2799 (1995)). These results indicate that the nonlinear, composition-dependent bandgap for the ternary nanocrystals is related to the behavior of the bulk system since these microscopic mechanisms are valid for both systems.

Figure 4:
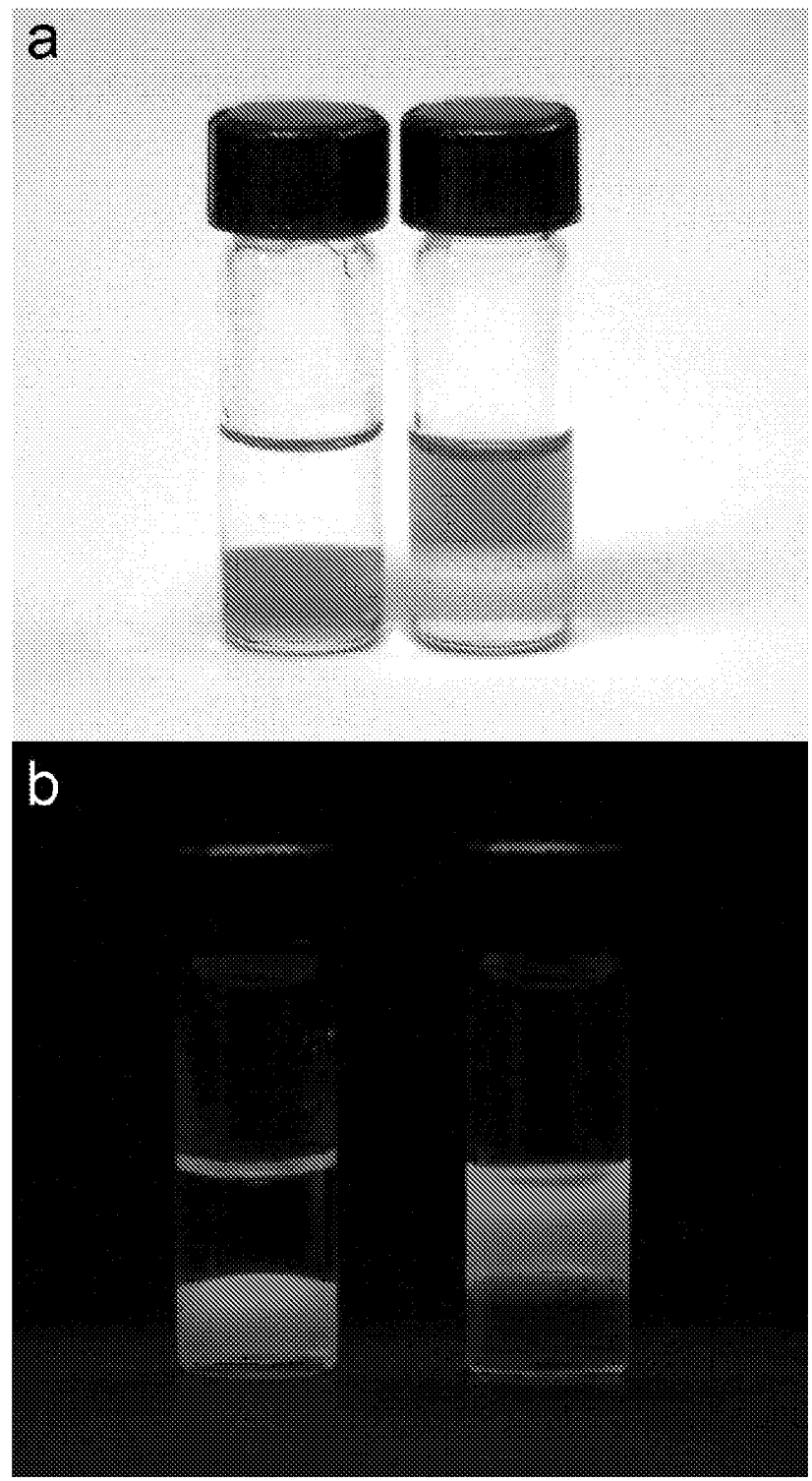
FIG. 4: Images of CdS-capped $CdSe_{1-x}Te_x$ quantum dots dispersed in chloroform (left vial) or dissolved in water (right vial) under (a) room light and (b) ultraviolet illumination. The fluorescence intensities were similar in chloroform and in water.

The PL quantum yields of all samples appeared to be composition-independent, ranging from about 15% to 20% for uncapped samples in chloroform. After capping the ternary nanocrystals with CdS, the PL quantum efficiencies increase to about 40-60% at room temperature. By using the procedure reported by Chan and Nie (Chan et al., *Science* 281: 2016-2018 (1998)), water-soluble $CdSe_{1-x}Te_x$ and CdS-capped $CdSe_{1-x}Te_x$ nanocrystals were prepared. The uncapped samples show a decrease in PL quantum efficiency which is similar to the behavior that has been well characterized for uncapped CdSe nanocrystals when using such procedures to obtain aqueous colloids (Aldana, et al., *J. Am. Chem. Soc.* 123, 8844-8850 (2001)). This problem is not seen in the case of capped quantum dots. No observable decrease was seen in the PL intensity as shown in the images shown in FIG. 4.

These core-shell nanocrystals are highly luminescent in biological buffer solution, but the colloids have a tendency to precipitate out of the solution after 2-3 weeks, most likely due to the desorption of the hydrophilic thiols that coat the surface. In order to maximize the stability of these aqueous colloids, the extent to which the number of cadmium sites on the surface could increase the long-term colloidal stability was examined. A series of $CdSe_{1-x}Te_x$ nanocrystals was synthesized with cadmium:chalcogen reactant ratios 5:1, 2:1, 1:1, 1:2 and 1:5. The nanocrystals were then submitted to the surface exchange procedure where the TOPO surface molecules were replaced by mercaptoacetic acid, and the nanocrystals were redispersed in an aqueous buffer (pH=8.5). The particle concentration was adjusted initially to 7.0 μM, and equal volumes of the initial samples were sealed in air-tight cuvettes and were stored at room temperature in the dark. Absorption measurements were taken at regular intervals over a period of 10 weeks to monitor the particle concentration. Care was taken to insure that precipitated particles were not disturbed or redispersed into the solvent by handling of the samples. Particle concentrations were calculated from the absorbance value at the first excitonic peak in the absorption spectrum.

Figure 5:
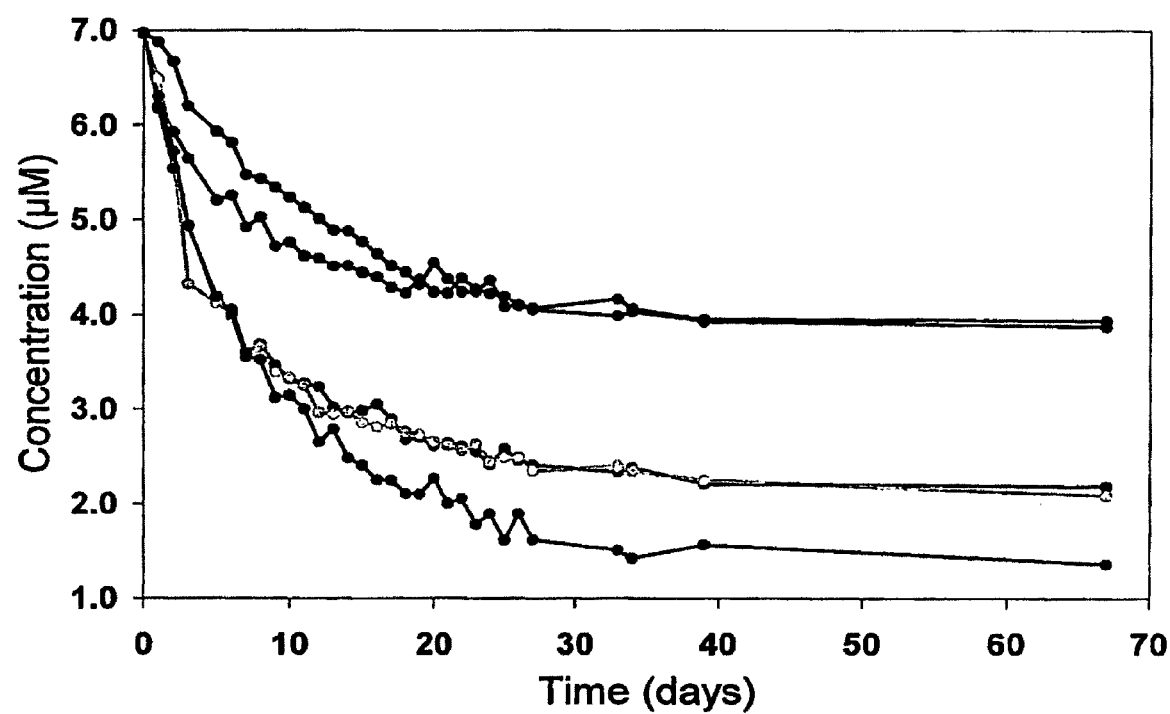
FIG. 5: Comparison of the long-term stability of water-soluble ternary quantum dots with varying degrees of cadmium excess on the particle surface. Samples were synthesized with an initial cadmium:chalcogen ratios of 5:1 (large cadmium excess, violet), 2:1 (cadmium excess, blue), 1:1 (equal cadmium and chalcogen, green), 1:2 (cadmium deficient, yellow), and 1:5 (large cadmium deficient, red).

All samples showed a similar trend of precipitation during an initial period of several days, but the stable particle concentrations showed a strong correlation with the richness of cadmium atoms on the nanocrystal surface (FIG. 5). This result indicates that the nanocrystal surface can be manipulated during synthesis in order to improve the colloid solution and potentially optical properties. Given the fact that the vast majority of methods for preparing bioconjugated quantum dots utilize one form or another of surface derivitization via cadmium-sulfur bonding, this finding concerning the nanocrystal surface is clearly of great practical importance.

In conclusion, a simple strategy for preparing robust and highly stable colloidal quantum dots that could serve as highly luminescent labels over a wide spectral range is reported herein. A nonlinear relationship is found between the emission wavelength and the nanocrystal composition. This nonlinear effect allows a broader range of spectral tuning than possible with the corresponding binary systems, effectively extending the useful range of accessible PL emission wavelengths (Recent work in our laboratory indicates that the tunable range can be extended to the near-infrared region by increasing the particle size. The longest wavelength we have observed is ~850 nm. Even broader spectral coverage could be obtained by using other ternary materials such as $CdS_{1-x}Se_x$, $CdS_{1-x}Te_x$, $ZnSe_{1-x}Te_x$, $Zn_{1-x}Cd_xTe$, $Cd_{1-x}Hg_xS$, etc.). As a result, $CdSe_{1-x}Te_x$ nanocrystals may be utilized as luminescent labels covering the entire visible spectrum and well into the near-infrared region. By keeping the particle size constant, the nanocrystals have the same surface curvature, the same surface area, and the same diffusion rate, all of which are advantageous for simplifying the number of experimental variables in multiplexed measurements. It is expected that luminescent ternary semiconductor quantum dots will find applications in medical diagnostics, high-throughput screening, multi-parameter cell labeling, and in-vivo optical imaging (Han et al., *Nat. Biotechnol.* 19: 631-635 (2001); Chan et al., *Curr. Opin. Biotechnol.* 13: 40-46 (2002); Bremer et al., *Nat. Med.* 7: 743-748 (2001); Becker et al., *Nat. Biotechnol.* 19: 327-331 (2001); Zaheer, et al., *Nat. Biotechnol.* 19: 1148-1154 (2001); and Sevick-Muraca et al., *Curr. Opin. Chem. Biol.* 6: 642-650 (2002)).

Example 5

This example demonstrates a method of producing a series of concentration-gradient quantum dots.

A 125 mL round-bottom flask containing 9 g TOPO, 3 g HDA and 16 mg CdO was heated to ~150° C. and was degassed under a vacuum of 20 Pa for 15 min. The flask was then filled with argon gas and its temperature was increased to 325° C. After the precursor CdO was dissolved completely in the solvent, the temperature was lowered to 300° C. and was allowed to stabilize for several minutes. For convenient control of reagent molar ratios, five premixed Se and Te solutions were prepared from the individual stock solutions at 0.4 M total concentration, but with Se:Te molar ratios of 100:0, 75:25, 50:50, 25:75, or 0:100. To prepare gradient quantum dots under cadmium-rich conditions, about 2.5 mL (0.25 mmol) of a premixed Se and Te stock solution (diluted 4 folds) was injected into a colorless TOPO/HDA solution containing 2.0 mmol cadmium at 300° C. Under these conditions, the cadmium precursor was in 8-fold excess of the total amount of injected Se and Te.

Example 6

This example demonstrates the characterization of the concentration-gradient quantum dots.

UV-VIS absorption spectra were recorded on a Shimadzu UV-2401 PC scanning spectrophotometer operating at a slit width of 1.0 nm. Bandgap energy determinations were made by analyzing the absorption data using the method outlined by Fendler and coworkers (Tian et al., *Phys. Chem.* 100: 8927-8939 (1996)) to extract the value for the absorption onset. Photoluminescence spectra were acquired on a Spex FluoroMax spectrometer. Emission spectra were taken using an excitation wavelength of 475 nm with excitation and emission slit widths set at 2.0 nm. Recorded spectra were corrected for the wavelength dependence of detector response. The optical densities of all samples were adjusted to between 0.10 and 0.15 at the excitation wavelength, and quantum yield measurements were made by comparing the integrated nanocrystal emission in chloroform with that of fluorescent dyes (Atto 565 and Atto 680, Fluka, Milwaukee, Wis.) in ethanol. Transmission electron micrographs were obtained on a JEOL 1210 electron microscope operating at an accelerating voltage of 90 kV. Samples were prepared by placing a dilute solution of nanocrystals in chloroform onto carbon-coated copper grids and allowing them to dry in a vacuum dessicator overnight.

Energy-dispersive x-ray (EDX) data were acquired on a Philips XL30 ESEM-FEG equipped with an EDAX light element detector, and processed on an EDAX *Phoenix* X-ray Microanalysis System. X-ray Diffraction data were obtained from powder samples of $CdSe_{1-x}Te_x$ nanocrystals, which were first precipitated in chloroform with methanol followed by centrifugation to isolate a nanocrystal pellet. Discarding the supernant, each pellet was allowed to dry overnight and then was crushed into a fine powder which was sealed in a 0.5 mm capillary and mounted on the platform goniometer such that the capillary axis was coincident with the main instrument axis. Data were collected using Mo Ka radiation with a weighted mean wavelength of 0.71073 A. The samples were continuously oscillated through 179 degrees about the instrument axis during a 90-second data collection period. Data were recorded with a Bruker-AXS SMART6000 two-dimensional CCD detector diffraction system and processed with Bruker's SMART and GADDS software to produce the standard intensity vs. diffraction angle data to a maximum diffraction angle of 39.5°.

Recent research indicated that elemental tellurium was considerably more reactive than selenium towards cadmium under rapid nucleation and growth conditions. Because of this difference in reactivity, the CdTe growth rate was approximately two times that of CdSe. These data were used to create a strategy for synthesizing concentration-gradient quantum dots. All reagents were added into a "single pot," with a precise control of the Se:Te molar ratios. The amount of injected cadmium was in large excess (by ca. 8-fold) relative to the total mole amounts of Se and Te. Under these conditions, the reagent in short supply was completely consumed while the reagent in large excess would maintain a nearly constant concentration during the entire course of the reaction. From both kinetic analysis and experimental measurements, it was shown that quantum dots with a gradient structure can be produced under cadmium-rich conditions (see FIG. 6).

Under cadmium-rich conditions, the difference in the intrinsic Se and Te reactivities was expected to result in quantum dots with a gradient alloy structure. During rapid particle nucleation and growth in hot TOPO, (Dabbousi et al., *J. Phys. Chem. B* 101: 9463-9475, (1997)); and Peng et al., *Am. Chem. Soc.* 119: 7019-7029 (1997)), the initial core is rich in Te due to its faster reaction rate toward cadmium. As the free Te was being depleted from the reaction mixture, CdSe deposition will become more important towards crystal growth. When all free Se and Te in the mixture were consumed, particle growth will stop-yielding alloyed quantum dots with a gradient Te concentration from the core to the surface. Because the outer layer was largely made of CdSe, this layer acts as an encapsulating shell for the CdTe-rich core. But unlike the traditional core-shell nanocrystals synthesized in two sequential steps, (Dabbousi et al., *J. Phys. Chem. B* 101: 9463-9475 (1997)); Peng et al., *Am. Chem. Soc.* 119: 7019-7029 (1997)), the gradient alloyed dots were prepared in a single step and did not have an abrupt boundary between the Te-rich core and the Se-rich shell. A potential problem not considered above was the so-called "Ostwald ripening" effect, (Peng, et al., *Am. Chem. Soc.* 120, 5343-5344, (1998); Desmet et al., *Langmuir*, 75, 2327-2332, (1999)), in which smaller particles or clusters are dissolved to feed the growth of larger ones. The net effect was be a composition averaging that renders the gradient dots more like the homogeneous dots. But this complication did not change the main conclusions of this work since growth is quenched before this mechanism becomes important.

Example 7

This example demonstrates a comparison study of alloyed semiconductor quantum dots, concentration-gradient quantum dots, and core-shell quantum dots.

Figure 6:
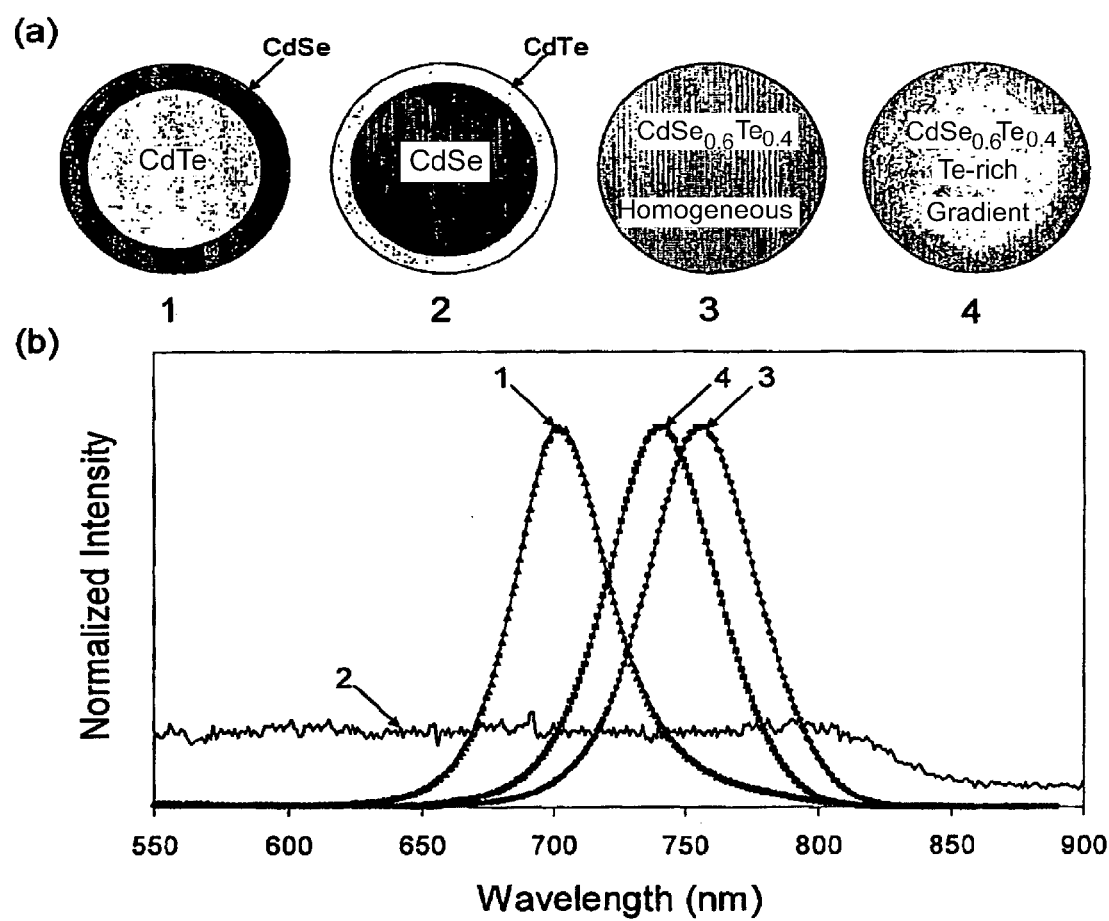
FIG. 6: Internal structures and optical properties of core-shell and alloyed $CdSe_{1-x}Te_x$ quantum dots, (a) Schematic drawings of four different types of quantum dots; and (b) corresponding fluorescence emission spectra. (1) Traditional core-shell CdTe—CdSe dots; (2) reversed core-shell dots; (3) homogeneous alloyed dots; and (4) gradient alloyed dots. All dots were synthesized to have a mean diameter of 5.9 nm (core plus shell) and an overall composition of $CdSe_{0.6}Te_{0.4}$, with relative standard deviations of ca. 10%. Within each batch of nanocrystals, the standard deviations for both size and composition were approximately 5%.

FIG. 6 shows the schematic structures of four different types of semiconductor quantum dots and their fluorescence emission spectra. The traditional CdTe-core/CdSe-shell quantum dots (FIG. 6 (1)) were synthesized by a two-step procedure, in which 4.5-nm CdTe cores were coated with a 0.7-nm CdSe shell. For the reverse core-shell structure (FIG. 6 (2)), 4.9-nm CdSe quantum dots were coated with a 0.5-nm CdTe layer. At these core sizes and shell thicknesses, the core-shell dots of both types had the same overall diameter of 5.9 nm and the same elemental composition of 60% Se and 40% Te. Calculations based on either crystal lattice parameters or bulk CdSe and CdTe densities[31] yielded composition results that were in excellent agreement (5%) with each other. Distinct from these core-shell structures, ternary alloyed quantum dots (FIG. 6 (3, homogeneous)) were prepared by using cadmium oxide and an 8-fold excess of a 75:25 (molar ratio) Se:Te stock solution as discussed above. Under these reaction conditions, the resulting quantum dots were found to have an elemental composition of 60% Se and 40% Te, same as the core-shell structures. The size of the ternary quantum dots was mainly controlled by the growth time, together with fine tuning of the nucleation rate at slightly different temperatures. Using a new stock solution of 60% Se and 40% Te and an 8-fold excess of cadmium oxide, a second type of ternary alloyed quantum dots (FIG. 6 (4, gradient)), was prepared for which the particle size was mainly controlled by the nucleation rate at different temperatures. The reaction was usually allowed to proceed to completion so that the gradient quantum dots would have the same Se:Te ratio as the stock solution.

These core-shell and alloy structures were similar to those of bimetallic Ag—Au nanoparticles, (Mulvany *Langmuir* 12: 788-800 (1996); Link et al., *J. Phys. Chem. B* 103: 3529-3533, (1999); Mallin et al., *NanoLett.* 2: 1235-1237 (2002)) and were supported by both elemental and structural data. With nearly identical sizes and compositions, how the internal structures (e.g., core-shell and alloys) of quantum dots would influence their optical properties were examined. As shown in FIG. 6 (*b*), the core-shell CdTe—CdSe nanocrystals were intensely fluorescent (emission peak at 702 nm), but the reversed core-shell CdSe—CdTe quantum dots showed little band-edge luminescence. This is not surprising because CdTe has a lower band gap than CdSe and does not provide an effective shell (leading to exciton recombination at surface trap sites). (Peng et al., *Am. Chem. Soc.* 123: 183-184 (2001); and Talapin et al., *Colloid Surf. A* 202: 145-154 (2002)). In comparison, both types of alloyed quantum dots were highly fluorescent, but their emission spectra were shifted to 741 nm for the gradient structure, and to 757 nm for the homogeneous structure. Remarkably, the alloyed quantum dots exhibited similar fluorescence efficiencies (QE=30-60%) and spectral widths (FWHM=35 nm) as the traditional core-shell dots (FWHM=30-35 nm). The high quantum yields and narrow spectral widths indicated that the alloyed quantum dots did not contain a heterogeneous population of amorphous clusters, but were highly crystalline in structure and monodisperse in size. Indeed, powder x-ray diffraction data (not shown) confirmed the crystalline wurtzite-type structure for the ternary particles at all compositions, ruling out the possibility of a phase change at intermediate compositions.

Figure 7:
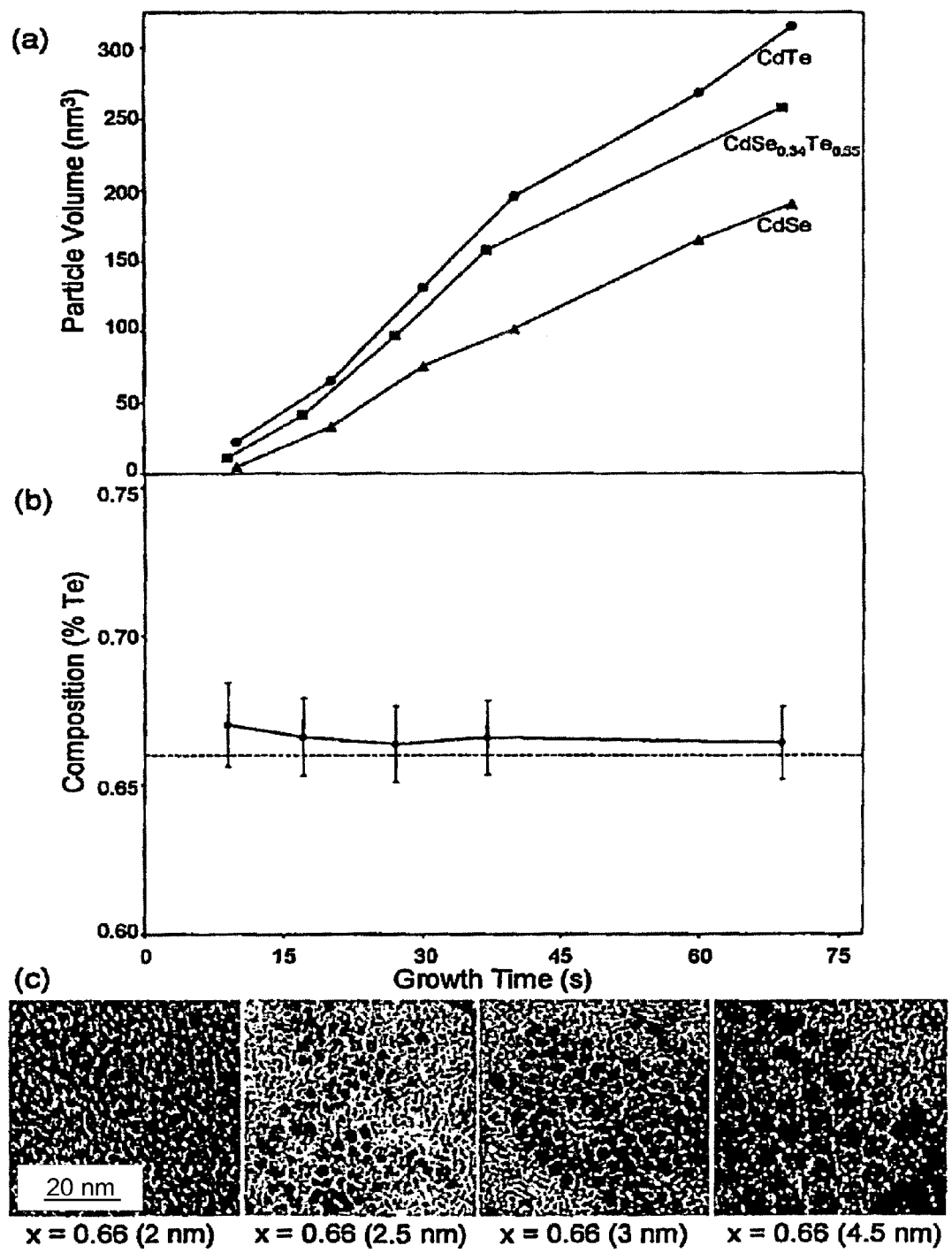
FIG. 7: Growth kinetics, elemental composition, and TEM structural data obtained from homogeneous $CdSe_{0.34}Te_{0.66}$ quantum dots during nanocrystal growth, (a) Plot of particle volume versus time; (b) plot of particle composition versus time; and (c) TEM images of alloyed quantum dots removed from the reaction mixture at different growth times. The symbol x is the mole fraction of tellurium in the alloy. See text for detailed discussion.

FIG. 7 shows results obtained from reaction kinetics, elemental composition, and transmission electron microscopy (TEM) studies. The kinetic data (FIG. 7(*a*)) indicate that the growth rate of CdTe is approximately double that of CdSe, and that the ternary dots grew at an intermediate rate depending on the exact composition and the reaction conditions. The elemental analysis data (FIG. 7(*b*)) revealed a nearly constant composition for the alloyed dots during the entire course of their growth. In fact, only a slight decrease of ca. 2% in Te composition was observed after extended periods of particle growth, during which the particle size increased from 2 nm to 8 nm. This decrease was reasonable because the total amount of Se and Te is only 8-fold in excess of cadmium (not infinite excess), so a small depletion will develop for Te with reaction time. This set of elemental data provides strong evidence that the ternary quantum dots have a homogeneous alloy structure that is nearly uniform from the start to the stop of particle growth. Furthermore, TEM data (FIG. 7(c)) demonstrate that at a constant composition of 66% Te, excellent size controls and size monodispersity could be achieved for the ternary quantum dots. In fact, the elemental composition data were in excellent agreement with the theoretical values predicted from the stock Se/Te molar ratios and their kinetic rates. For example, it was found that under cadmium-limited conditions, injected Se/Te ratios of 75:25, 50:50 and 25:75 resulted in nanocrystal compositions of 61:39, 34:66 and 15:85, which were nearly identical to the predicted values of 60:40, 33:67, and 14:86.

Figure 8:
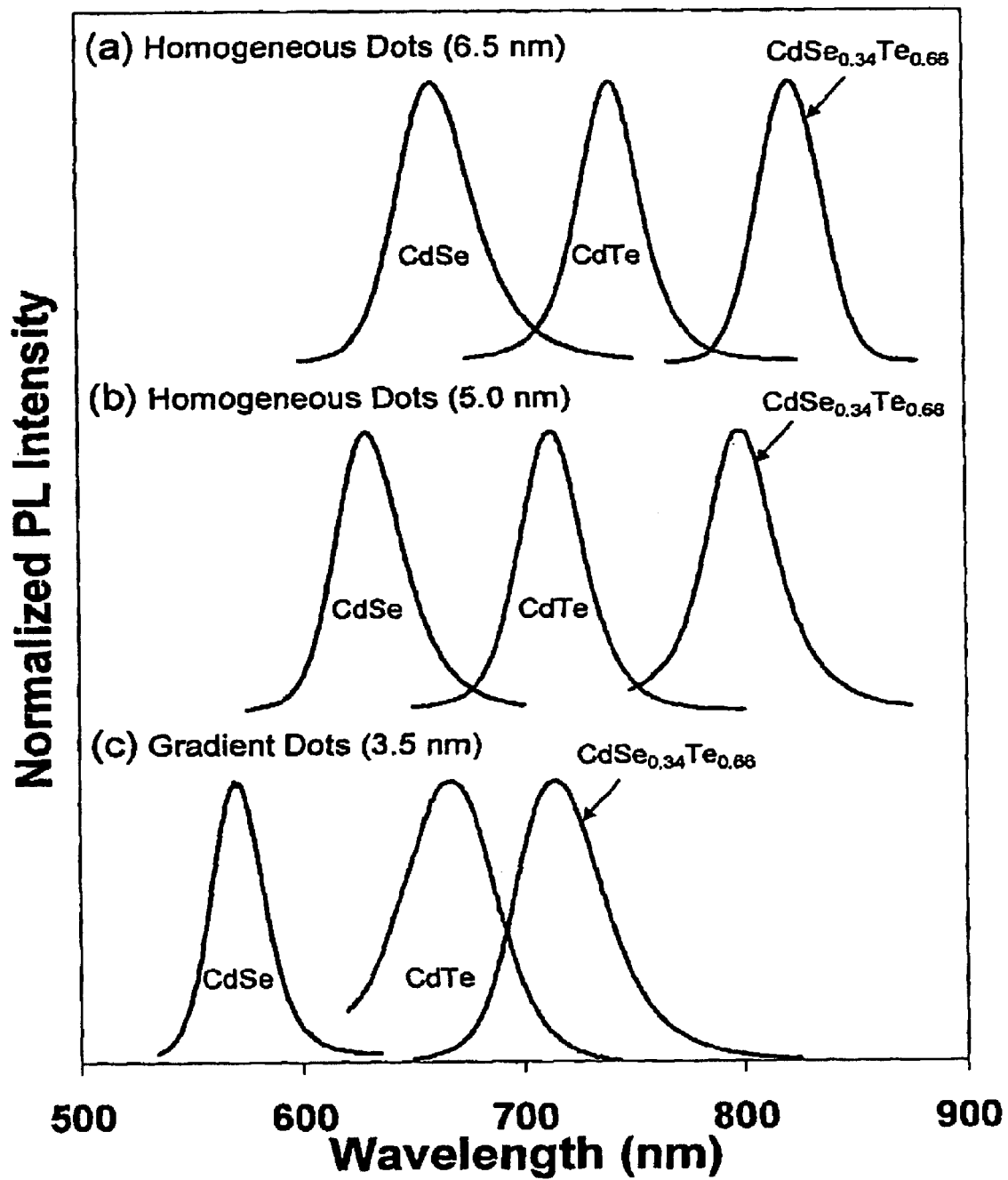
FIG. 8: Comparison of the emission spectra among CdSe, CdTe, and $CdSe_{0.34}Te_{0.66}$ quantum dots at three particle sizes. For each size series (a)-(c), the binary dots and the alloyed dots (either homogeneous or gradient) were synthesized to have the same overall diameter (accurate to within 5-10%). (d): TEM images of 5-nm quantum dots (constant size) with different compositions.
Figure 8:
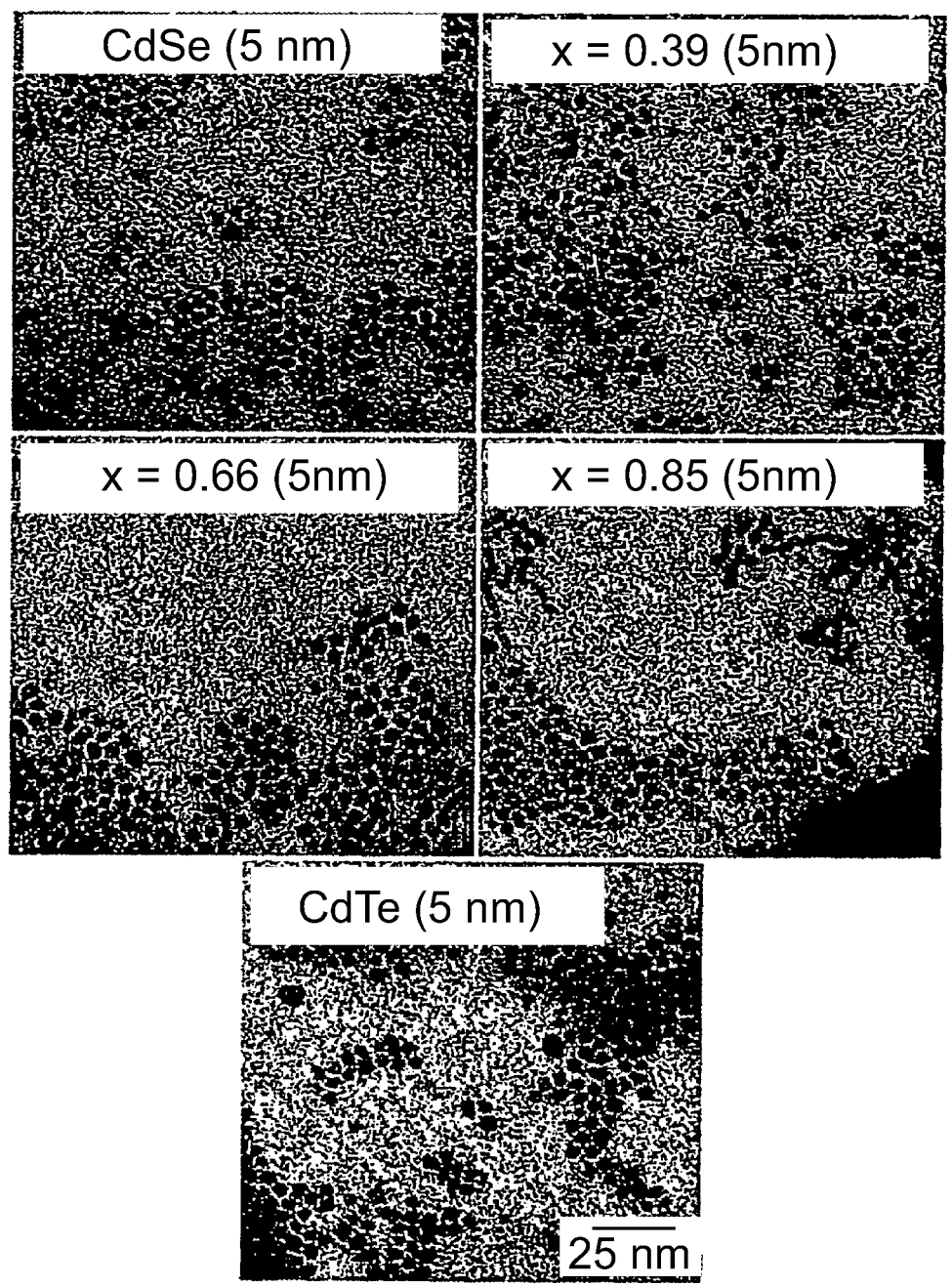

Further evidence for the alloyed internal structures was that the quantum dots could be tuned to emit light outside of the wavelength ranges defined by the binary CdSe and CdTe nanocrystals. FIG. 8 shows the fluorescence spectra obtained from three size series (sets) of CdSe, CdTe, and $CdSe_{1-x}Te_x$ quantum dots. In the 3.5-nm size series, the gradient alloyed dots emitted fluorescent light that was 145 nm longer than the binary CdSe dots and 50 nm longer than the binary CdTe dots. In the 5.0-nm and 6.5-nm size series, the emission spectra of the homogeneous alloyed dots were red-shifted to ca. 800 nm and 825 nm, respectively. In each of these size series, the particle sizes were constant within 5-10 percent, as judged by the TEM data (FIG. 8 (d)). In the worst case scenario, the size of the CdTe dots were 10% larger than the mean (5.0 nm) and the size of the CdSeTe dots were 10% smaller than the mean. The emission wavelength of the largest CdTe dots (5.5 nm) was expected to be 730 nm, which is still shorter than the emission peak (780 nm) of the smallest CdSeo.34Teo.66 dots (4.5 nm). This simple statistical analysis ruled out particle size variations as the cause of the large spectral shifts observed in FIG. 3.

Figure 9:
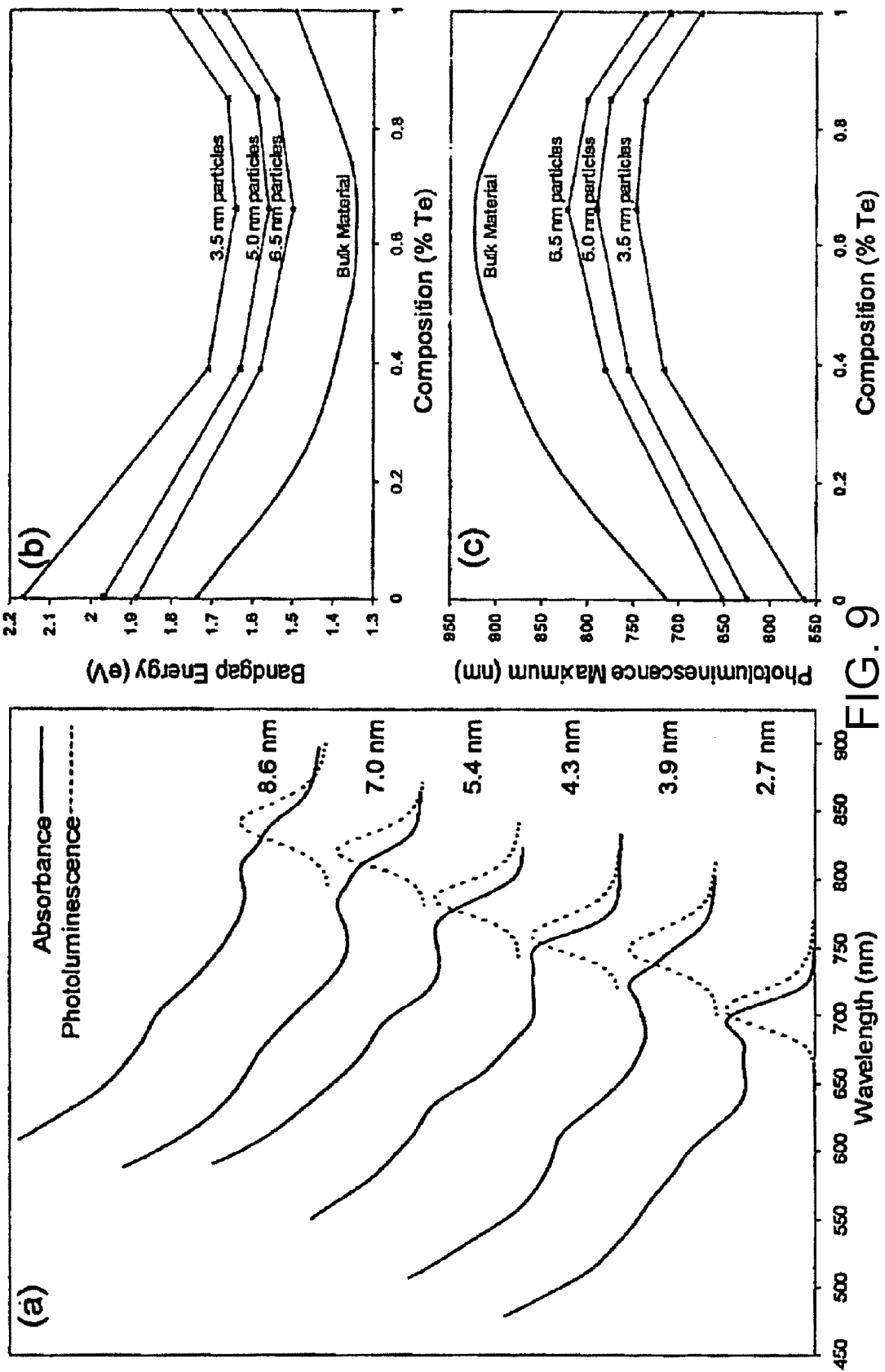
FIG. 9: Relationships between the composition and the absorption/emission energies for homogeneous $CdSe_{1-x}Te_x$ quantum dots at different sizes, (a) UV-Vis absorption and photoluminescence spectra of $CdSe_{0.34}Te_{0.66}$ quantum dots in the size range of 2.7-8.6 nm; (b) plots of the absorption onset energy (in eV) as a function of tellurium content; and (c) plots of the emission peak wavelength (nm) as a function of tellurium content. Note that the absorption onsets are slightly lower in energy than the emission maxima.
Figure 10:
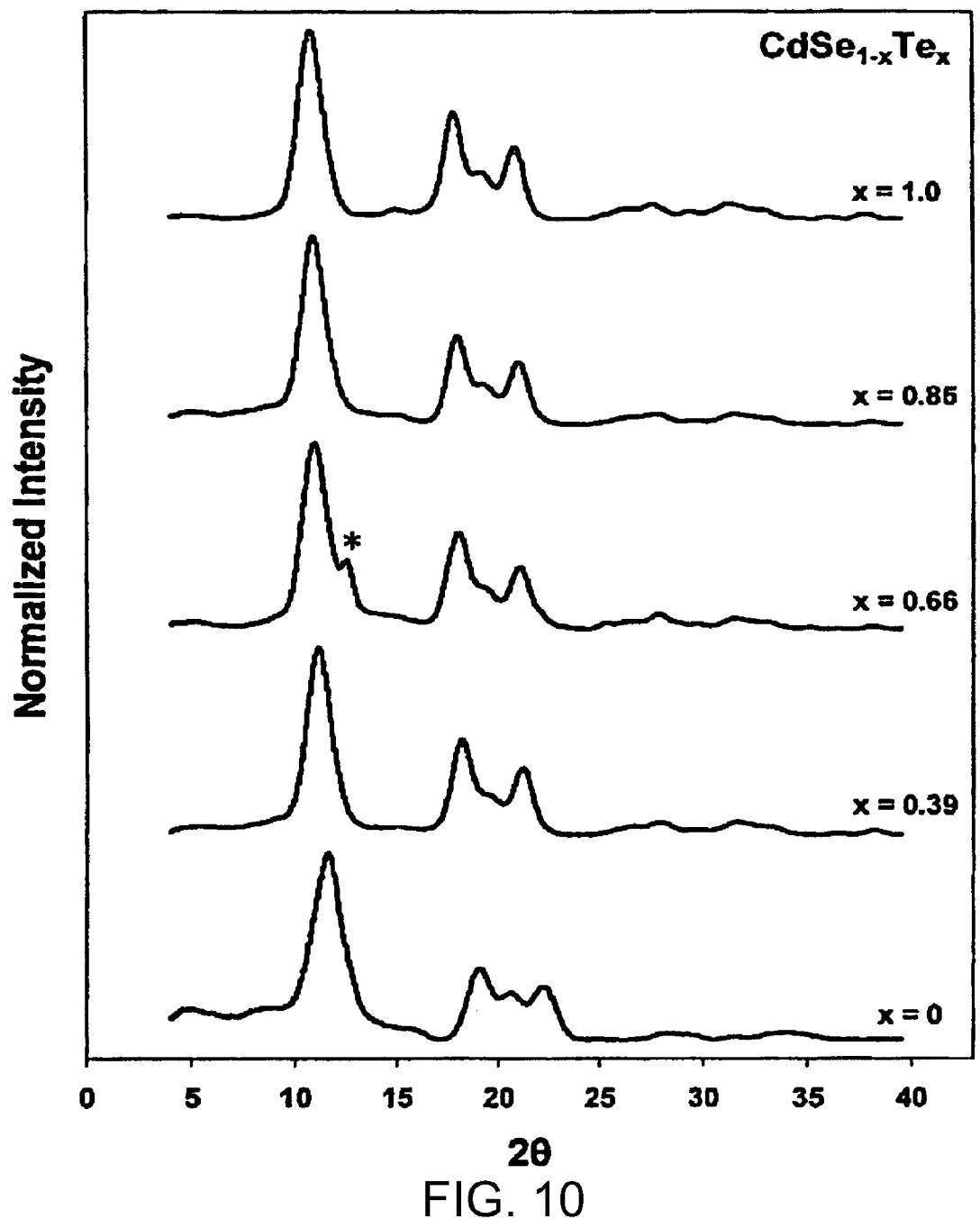
FIG. 10: X-ray power diffraction data obtained from pure CdSe, pure CdTe, and alloyed $CdSe_{1-x}Te_x$ quantum dots. The size of all dots was approximately 5 nm in diameter, and the asterisk (*) indicates a spurious signal.

To investigate the composition effect in a more quantitative manner, alloyed quantum dots in a broad range of sizes and compositions were prepared and characterized. FIG. 9 compares the absorption and fluorescence spectra for these dots, and further shows the relationships between the composition and the absorption/emission energies. The bulk data are also included for comparison. (Willardson and Goering (Eds.) *Compound Semiconductors*, Reinhold, New York, (1962)). The absorption and emission data showed several resolved electronic transitions and clear band-edge fluorescence emission, analogous to those reported for high-quality binary quantum dots, (Peng et al., *Am. Chem. Soc.* 123: 183-184 (2001); and Talapin et al., *Colloid Surf. A* 202: 145-154 (2002)). The plots, however, revealed a striking nonlinear relationship between the composition and the excitonic absorption and band-edge emission. This nonlinear relationship explained the unusually large spectral shifts reported in FIG. 8. In fact, alloyed quantum dots with a tellurium composition between 30% and 100% should have emitted light at longer wavelengths than the parent CdSe and CdTe dots. Also, it was clear that the homogeneous alloyed dots of all sizes followed a similar nonlinear curve, reaching the lowest energy point at ~60% tellurium content.

Previous studies of bulk semiconductor alloys have reported a similar nonlinear effect, called "optical bowing. (Willardson and Goering (Eds) *Compound Semiconductors*, Reinhold, New York, (1962); and Poon et al., *Phys. Condensed Matter* 7: 2783-2799 (1995)). The bandgap reduction observed in CdSeTe is particularly pronounced in comparison with other members of this alloy family. It is, thus, likely that the same mechanisms are operative in both the macroscopic and nanoscopic materials. In a theoretical model developed by Zunger and coworkers, (Bernard et al. A. *Phys. Rev. B* 36: 3199-3226 (1987); and Wei et al., *Appl. Phys.* 87: 1304-1311 (2000)), the observed nonlinear effect could be explained and even predicted by considering that different ions in the alloy have different atomic sizes, different electronegativity values, and different lattice constants. In particular, relaxation of the anion-cation bonds to their equilibrium positions led to local structural ordering and a significant bandgap reduction.

It is worth noting that bulk alloying has been used to develop high-strength materials for mechanical applications (e.g., aircrafts), biocompatible materials for medical implants, and a broad range of semiconductor materials for optoelectronic applications (e.g., diode lasers and detectors). For alloyed nanostructures, these results demonstrate that three factors (particle size, composition, and internal structure) can be used to control the quantum confinement effect, providing new or novel properties not available from individual components. This insight opens the possibility of developing a variety of ternary and quaternary semiconductor quantum dots based on both II-VI and III-VI materials. (Willardson and Goering (Eds) *Compound Semiconductors*, Reinhold, New York, (1962)).

Due to their far-red and near-infrared fluorescence properties, the alloyed quantum dots are well suited for applications in in-vivo molecular imaging (Weissleder et al., *NatureBiotechnol.* 17: 375-378 (1999); Bremer et al., *Nat. Med.* 7: 743-748 (2001); Becker et al., *Nat. Biotechnol.* 19: 327-331 (2001); Zaheer et al., *Nat. Biotechnol.* 19: 1148-1154 (2001); Sevick-Muraca et al., *Curr. Opin. Chem. Biol.* 6: 642-650 (2002)), and ultrasensitive biomarker detection. (McWhorter et al., *Electrophoresis* 21: 1267-1280 (2000); and Patonay et al., *Anal. Chem.* 63: A321-A326 (1991)). Visible light has been used for cellular imaging and tissue diagnosis, (Sokolov et al., *Curr. Opin. Chem. Biol.* 6: 651-658 (2002); and Brown et al., *Nat. Med.* 7: 866-870 (2001)) but optical imaging of deeper tissues (millimeters) requires the use of far-red or near-infrared light in the spectral range of 650-900 nm. This wavelength range provides a "clear" window for in-vivo optical imaging because it is separated from the major absorption peaks of blood and water. In comparison with traditional organic fluorophores, (Weissleder et al., *NatureBiotechnol.* 17: 375-378 (1999); Bremer et al., *Nat. Med.* 7: 743-748 (2001); Becker et al., *Nat. Biotechnol.* 19: 327-331 (2001); Zaheer et al., *Nat. Biotechnol.* 19: 1148-1154 (2001); Sevick-Muraca et al., *Curr. Opin. Chem. Biol.* 6: 642-650 (2002); McWhorter et al., *Electrophoresis* 21: 1267-1280 (2000); Patonay et al., *Anal. Chem.* 63: A321-A326 (1991); Sokolov et al., *Curr. Opin. Chem. Biol.* 6: 651-658 (2002); and Brown et al., *Nat. Med.* 7: 866-870 (2001)), near-infrared-emitting quantum dots should allow more sensitive biomolecular detection and multicolor optical imaging. Under photon-limited in vivo conditions (where light intensities are severely attenuated by scattering and absorption), the large absorption coefficients of quantum dots (on the order of $10^6$ cm$^{-1}$M$^{-1}$, ca. 10-20 times larger than those of common organic dyes) will be essential for efficient probe excitation. Unlike current single-color molecular imaging, multi-wavelength optical imaging with quantum dots will allow intensity ratioing, spatial colocalization, and quantitative target measurements at single metastasized tumor sites and for single anatomical structures. For these biological applications, it is noted that the alloyed quantum dots can be made water-soluble and biocompatible by using the surface-modification and cross-linking procedures reported for CdSe and CdTe binary quantum dots. (Bruchez et at., *Science* 281: 2013-2015 (1998); Chan et al., *Science* 281: 2016-2018 (1998); Akerman et al., *Proc. Natl. Acad. Sci. USA* 99: 12617-12621 (2002); Dubertret et al., *Science* 298: 1759-1762 (2002); Wu et al., *Nat. Biotechnol.* 21: 41-46 (2003); and Jaiswal et al., *Nat. Biotechnol.* 21: 47-51 (2003)). Their optical properties such as spectral width, quantum yields, and photostability are similar to those of the original materials.

In conclusion, reported herein is a novel procedure for preparing large quantities of alloyed semiconductor quantum dots (CdSeTe) for continuous tuning of quantum confinement without changing the particle size. In addition to particle size, these results demonstrate that two new parameters, composition and internal structure, are available for tuning the optical and electronic properties of alloyed semiconductor quantum dots. The concept of composition tuning is of course not new, but we have achieved perhaps the first demonstration of how this concept works in a colloidal semiconductor system. With broadly tunable optical and electronic properties, this new class of alloyed quantum dots should open exciting possibilities in designing novel nanostructures and in developing near-infrared-emitting probes for multiplexed optical encoding and in-vivo molecular imaging. Han et al., *Nat. Biotechnol.*, 19, 631-635 (2001); Chan et al., *Current Opinion Biotech.* 13, 40-46 (2002).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of producing a ternary concentration-gradient quantum dot comprising an alloy of a first semiconductor AB and a second semiconductor AC, wherein A is a species that is common to the first semiconductor and the second semiconductor and B and C are each a species found in only one of the first semiconductor and the second semiconductor, and wherein the alloy comprises CdSeTe and has a molecular formula $CdSe_{1-x}Te_x$, the alloy comprises CdSSe and has a molecular formula $CdS_{1-x}Se_x$, the alloy comprises CdSTe and has a molecular formula $CdS_{1-x}Te_x$, the alloy comprises ZnSeTe and has a molecular formula $ZnSe_{1-x}Te_x$, the alloy comprises ZnCdTe and has a molecular formula $Zn_{1-x}Cd_xTe$, the alloy comprises CdHgS and has a molecular formula $Cd_{1-x}Hg_xS$, the alloy comprises HgCdTe and has a molecular formula HgCdTe, the alloy comprises InGaAs and has a molecular formula InGaAs, the alloy comprises GaAlAs and has a molecular formula GaAlAs, or the alloy comprises InGaN and has a molecular formula InGaN, wherein x is any fraction between 0 and 1, which method comprises:
   (i) providing a first solution under conditions which allow nanocrystal formation to take place,
   (ii) providing a second solution comprising A, B, and C at a molar ratio under conditions which do not allow nanocrystal formation to take place, wherein each of B and C are present in the second solution at a concentration that is reaction-limiting,
   (iii) adding the second solution to the first solution, thereby allowing nanocrystal formation to take place, and
   (iv) changing the conditions to conditions that halt nanocrystal growth and formation.

2. The method of claim 1, wherein the first semiconductor is selected from the group consisting of ZnSe, ZnTe, CdS, CdSe, CdTe, HgS, HgTe, GaAs, and InAs.

3. The method of claim 1, wherein the second semiconductor is selected from the group consisting of ZnSe, ZnTe, CdS, CdSe, CdTe, HgS, HgTe, GaAs, and InAs.

4. A method of producing a series of ternary concentration-gradient quantum dots, wherein each of the quantum dots comprises an alloy of a first semiconductor AB and a second semiconductor AC, wherein A is a species that is common to the first semiconductor and the second semiconductor and B and C are each a species found in only one of the first semiconductor and the second semiconductor, and wherein the alloy comprises CdSeTe and has a molecular formula $CdSe_{1-x}Te_x$, the alloy comprises CdSSe and has a molecular formula $CdS_{1-x}Se_x$, the alloy comprises CdSTe and has a molecular formula $CdS_{1-x}Te_x$, the alloy comprises ZnSeTe and has a molecular formula $ZnSe_{1-x}Te_x$, the alloy comprises ZnCdTe and has a molecular formula $Zn_{1-x}Cd_xTe$, the alloy comprises CdHgS and has a molecular formula $Cd_{1-x}Hg_xS$, the alloy comprises HgCdTe and has a molecular formula HgCdTe, the alloy comprises InGaAs and has a molecular formula InGaAs, the alloy comprises GaAlAs and has a molecular formula GaAlAs, or the alloy comprises InGaN and has a molecular formula InGaN, wherein x is any fraction between 0 and 1, which method comprises:
   (i) providing a first solution under conditions which allow nanocrystal formation to take place,
   (ii) providing a second solution comprising A, B, and C at a molar ratio under conditions which do not allow nanocrystal formation to take place, wherein each of B and C are present in the second solution at a concentration that is reaction-limiting, (iii) adding the second solution to the first solution, thereby allowing nanocrystal formation to take place,
(iv) changing the conditions to conditions that halt nanocrystal growth and formation, and
(v) repeating steps (i)-(iv) at least one time, thereby producing at least one other quantum dot of the series, wherein each time the molar ratio of A, B, and C is different from the molar ration ratio of A, B, and C of the other quantum dots of the series.

5. The method of claim 4, wherein the first semiconductor is selected from the group consisting of ZnSe, ZnTe, CdS, CdSe, CdTe, HgS, HgTe, GaAs, InAs.

6. The method of claim 4, wherein the second semiconductor is selected from the group consisting of ZnSe, ZnTe, CdS, CdSe, CdTe, HgS, HgTe, GaAs, and InAs.

7. The method of claim 1, wherein the first semiconductor is CdSe and the second semiconductor is CdTe.

8. The method of claim 4, wherein the first semiconductor is CdSe and the second semiconductor is CdTe.

9. The method of claim 1, wherein the first semiconductor is CdS and the second semiconductor is CdSe.

10. The method of claim 1, wherein the first semiconductor is CdS and the second semiconductor is CdTe.

11. The method of claim 1, wherein the first semiconductor is CdS and the second semiconductor is HgS.

12. The method of claim 4, wherein the first semiconductor is CdS and the second semiconductor is CdSe.

13. The method of claim 4, wherein the first semiconductor is CdS and the second semiconductor is CdTe.

14. The method of claim 4, wherein the first semiconductor is CdS and the second semiconductor is HgS.

* * * * *